United States Patent
Salman et al.

(10) Patent No.: US 9,968,242 B2
(45) Date of Patent: May 15, 2018

(54) SUCTION CONTROL UNIT FOR AN ENDOSCOPE HAVING TWO WORKING CHANNELS

(71) Applicant: EndoChoice, Inc., Alpharetta, GA (US)

(72) Inventors: Golan Salman, Atlit (IL); Amram Aizenfeld, Ramot Menashe (IL); Stephan Wieth, Klein Nordende (DE); Alexander Lang, Wedel (DE); Tracy Knapp, Snellville, GA (US); Justin Wolfe, Lawrenceville, GA (US)

(73) Assignee: ENDOCHOICE, INC., Alpharetta, GA (US)

( * ) Notice: Subject to any disclaimer, the term of this patent is extended or adjusted under 35 U.S.C. 154(b) by 753 days.

(21) Appl. No.: 14/573,691

(22) Filed: Dec. 17, 2014

(65) Prior Publication Data

US 2015/0182105 A1 Jul. 2, 2015

Related U.S. Application Data

(60) Provisional application No. 61/917,530, filed on Dec. 18, 2013, provisional application No. 61/969,649, filed on Mar. 24, 2014.

(51) Int. Cl.
*A61B 1/018* (2006.01)
*A61B 1/015* (2006.01)
(Continued)

(52) U.S. Cl.
CPC .......... *A61B 1/015* (2013.01); *A61B 1/00068* (2013.01); *A61B 1/00137* (2013.01);
(Continued)

(58) Field of Classification Search
CPC . A61B 1/00068; A61B 1/00137; A61B 1/015; A61B 1/018; A61B 17/3498;
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Notice of Allowance dated May 25, 2017 for U.S. Appl. No. 14/318,189.
(Continued)

*Primary Examiner* — Timothy J Neal
*Assistant Examiner* — Aaron B Fairchild
(74) *Attorney, Agent, or Firm* — Bookoff McAndrews, PLLC

(57) ABSTRACT

A suction control unit placed on an endoscope to control application of suction through at least one of two working channels of the endoscope. The suction unit has first and second valves with first and second valve openings, at a proximal end, that lead through to a distal end, which is adapted to be placed on the first and second ports of the two working channels. The suction unit has a channel extending between the first and second valves, an opening extending from a front wall to a rear wall of the housing and through the channel, and a switcher having a handle and a shaft with a through hole. When the shaft is placed within the opening and in a first position, suction is applied to both the working channels. When the shaft is placed within the opening and in a second position, suction is applied to only one of the two working channels.

22 Claims, 16 Drawing Sheets

(51) Int. Cl.
  *A61B 1/00* (2006.01)
  *A61M 25/00* (2006.01)
  *A61M 1/00* (2006.01)
  *A61B 17/34* (2006.01)
  *A61M 39/22* (2006.01)
  *A61M 39/24* (2006.01)
  *A61M 39/26* (2006.01)

(52) U.S. Cl.
  CPC ........... *A61B 1/018* (2013.01); *A61M 1/0035* (2014.02); *A61B 17/3498* (2013.01); *A61M 25/0028* (2013.01); *A61M 39/22* (2013.01); *A61M 2039/229* (2013.01); *A61M 2039/248* (2013.01); *A61M 2039/2473* (2013.01); *A61M 2039/268* (2013.01)

(58) Field of Classification Search
  CPC ........... A61M 1/0035; A61M 25/0028; A61M 39/22; A61M 2039/229; A61M 2039/2473; A61M 2039/248; A61M 2039/268
  See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | MayerIII |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |

(56) References Cited

U.S. PATENT DOCUMENTS

| | | |
|---|---|---|
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0088199 A1* | 4/2007 | Ito ................. A61B 1/00137 600/156 |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |

(56) References Cited

U.S. PATENT DOCUMENTS

| | | |
|---|---|---|
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |

(56) References Cited

FOREIGN PATENT DOCUMENTS

| | | |
|---|---|---|
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated May 23, 2017 for U.S. Appl. No. 14/500,975.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.

(56) References Cited

OTHER PUBLICATIONS

Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
International Search Report for PCT/US2014/071085, dated Mar. 27, 2015.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action date Feb. 26, 2016 for U.S. Appl. No. 14/274,323.
Office Action dated Feb. 4, 2016 for U.S. Appl. No. 14/271,234.

* cited by examiner

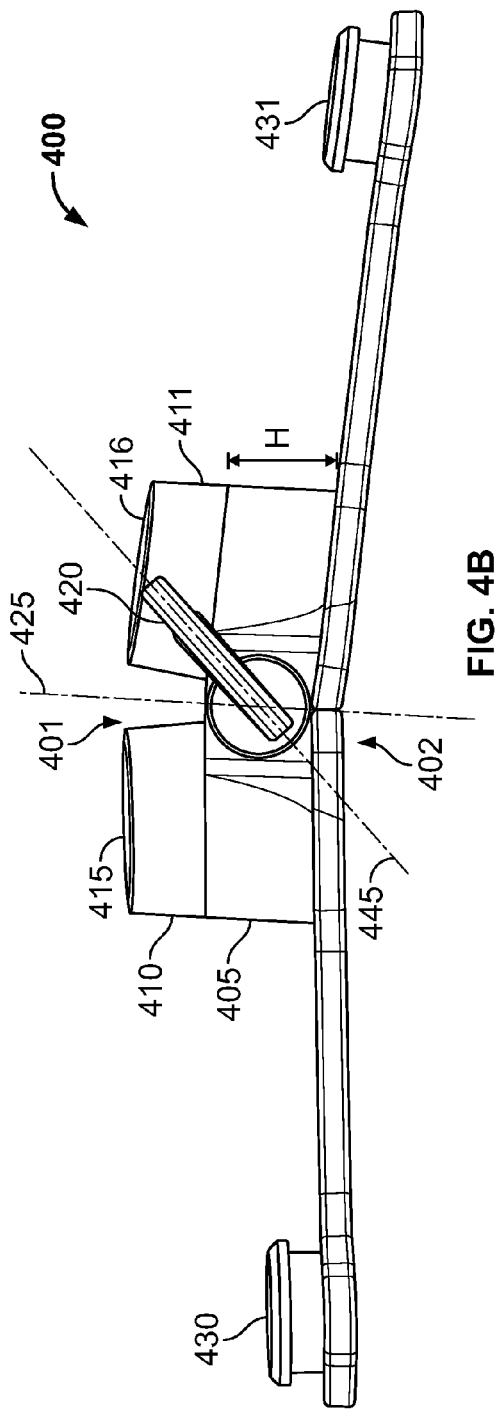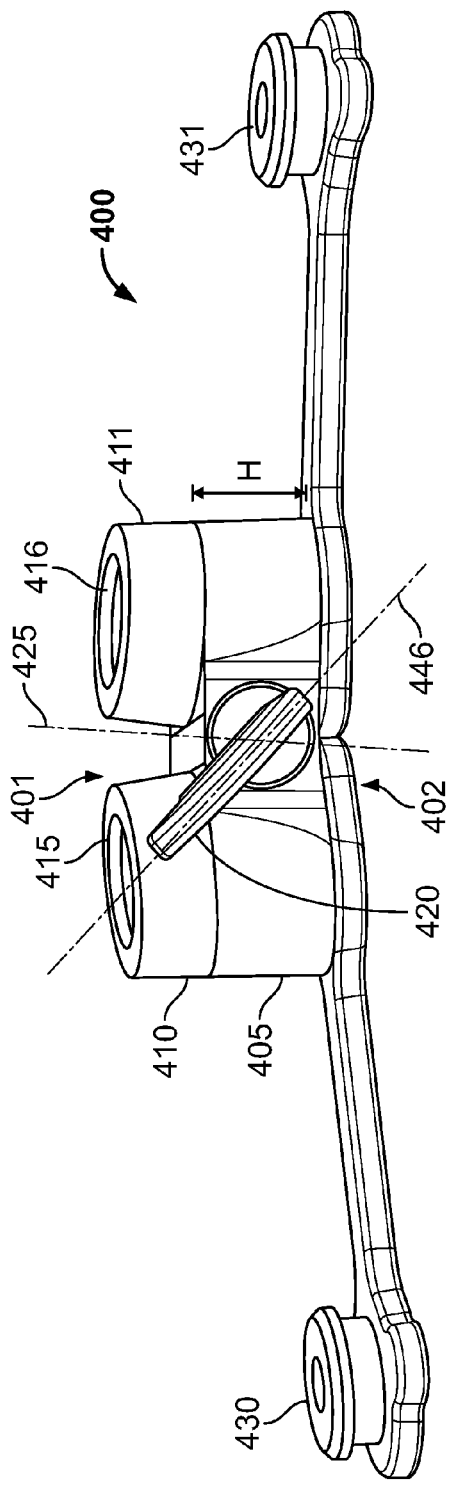

SUCTION CONTROL UNIT FOR AN ENDOSCOPE HAVING TWO WORKING CHANNELS

CROSS-REFERENCE TO RELATED APPLICATIONS

The present invention relies upon, for priority, the following patents and/or applications:

U.S. Provisional Patent Application No. 61/917,530 entitled "A Suction Control Unit for An Endoscope Having Two Working Channels" and filed on Dec. 18, 2013; and U.S. Provisional Patent Application No. 61/969,649 entitled "A Suction Control Unit for An Endoscope Having Two Working Channels" and filed on Mar. 24, 2014.

All of the above-mentioned applications are herein incorporated by reference in their entirety.

FIELD

This invention relates generally to an endoscopy system. More particularly, this invention relates to a suction control unit that controls, enables or allows for suction through one or both of two working channels of an endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper gastrointestinal endoscopy and others. Endoscopes may be inserted into the body's natural orifices or through an incision in the skin. Endoscopes may be rigid or flexible and typically have optical and illuminating features that allow a physician to view the work site. Often during such procedures, it becomes necessary for the physician to evacuate blood clots, mucus, waste or other materials in a body cavity to clear the field of view.

Endoscopes provide limited access to medical tools through a single working channel. To allow for extended access of medical tools, multiple working channels would be advantageous. One such endoscope has been described in U.S. patent application Ser. No. 13/413,252, entitled "Multi Camera Endoscope Assembly Having Multiple Working Channels", filed on Mar. 6, 2012 by the present Applicant, wherein the endoscope assembly comprises "at least one front-pointing camera and at least one front illuminator associated therewith, at least one side-pointing camera and at least one of side illuminator associated therewith, a first front working channel configured for insertion of a medical tool and a second front working channel configured for insertion of a medical tool."

Endoscopes typically have valves located at a control unit, also referred to as an endoscope handle for the physician to control a suction line and an air/water line. Conventionally, a physician would use the suction line to clear blood clots, mucus, wastes, among other things. However, with prior art suction line and/or the associated valve, when solid substances or substances with high viscosity (such as coagulated blood, tissue pieces, mucus, wastes and the like) are to be suctioned from inside the body, there are problems that a large load is applied and a passage inside the valve might be clogged by the suctioned substances.

Accordingly, there is a need for a suction control unit that can manage high suction load when substances with high viscosity, large size, or large amount of fluid, such as coagulated blood, tissue pieces, mucus, and wastes, in the lumen are suctioned. There is a need for a suction control unit that can take advantage of two working channels to manage high suction load when needed, and switch to allowing suction through only one of the two working channels when the suction load is low. Thus there is need for the suction control unit to selectively allow for suction to be applied through one or both of the two working channels while a surgical/treatment tool may or may not be inserted through one or both of the two working channels.

SUMMARY

The following embodiments and aspects thereof are described and illustrated in conjunction with systems, tools and methods, which are meant to be exemplary and illustrative, not limiting in scope.

There is provided herein, according to an embodiment of the invention, a suction control unit configured to be detachably attached to at least two working channels of an endoscope and control application of suction through at least one of the two working channels, the suction unit including a) a housing defined by a central longitudinal axis and having a first valve and a second valve positioned on either side of the central longitudinal axis, wherein a proximal end of the first and the second valve has respective first and second valve openings that lead through to a distal end of the first and the second valve, and wherein the distal end of the first and the second valve is configured to be detachably attached to first and second ports of the two working channels; a channel extending between the first and the second valve within the housing, wherein a channel axis is substantially perpendicular to the central longitudinal axis of the housing; an opening extending from a front wall to a rear wall of the housing and through the channel between the first and the second valve; and b) a switcher having a handle and a shaft extending from the handle along a long axis, wherein the shaft has a through hole such that a hole axis is substantially perpendicular to the long axis, wherein when the shaft is placed within the opening and turned to a first position, the hole axis aligns with the channel and thereby opens the channel, enabling suction to be applied to both of the two working channels, and wherein, when the shaft is placed within the opening and turned to a second position, the shaft blocks the channel and causes suction to be applied to only one of the two working channels.

There is also provided herein, according to another embodiment of the invention, a suction control unit configured to be detachably attached to two working channels of an endoscope and control an application of suction through at least one of said two working channels, the suction unit including a) first and second valves having a proximal end and a distal end, wherein the proximal end has first and second valve openings that lead through to the distal end, wherein the distal end retains first and second plugs, and wherein the distal end is adapted to be detachably attached to first and second ports of the two working channels; b) a housing having first and second receptacle tubes, on either side of a longitudinal axis of the housing, holding the first and second valves therein; a channel extending between the first and second receptacle tubes to enable fluid communication between the first and second valves held within the first and second receptacle tubes, wherein a channel axis is substantially perpendicular to the longitudinal axis; an opening extending from a front wall to a rear wall of the housing and through the channel; and c) a switcher having a handle and a shaft extending from the handle along a long axis, wherein the shaft has a plurality of pins and a through hole such that a hole axis is substantially perpendicular to the long axis, wherein the shaft is placed within the opening, and wherein a first position of the switcher causes suction to be applied to both the working channels and a second position of the switcher causes suction to be applied to one of the two working channels.

In an embodiment, the first and second valves, the housing and the switcher can be disassembled into independent units and reassembled when required. Optionally, outer walls of the first and second valves have depressions to enable flush fit of the valves with the housing when assembled.

Optionally, the first and second positions are respectively at about 45 degrees on either side of the longitudinal axis of the housing. In one embodiment, switcher tracks are located on the front and the rear wall of the housing to restrict rotation of the switcher beyond the first and second positons. In another embodiment, upper and lower tracks are located on at least the front wall to engage with the plurality of pins and restrict rotation of the switcher beyond said first and second positions.

According to an embodiment, in the first position the hole axis is substantially parallel to the channel axis while in the second position the hole axis is substantially perpendicular to the channel axis.

According to an embodiment, the shaft of the switcher has a first surface that abuts against the front wall and a second surface that protrudes from and abuts against the rear wall. In an embodiment, the first surface is ring shaped and the second surface has a semi-spherical shape. In an embodiment, a first number of the plurality of pins abut against the first surface and a second number of the plurality of pins abut against the second surface.

Optionally, the handle of the switcher has an open ring to hold two stoppers configured for the first and the second valve openings.

In another embodiment, the first and second surfaces are ring shaped and the second surface has a cylindrical or rectangular extension with two open rings to respectively hold two stoppers configured for the first and the second valve openings.

According to an embodiment, a surgical tool is inserted in one or both of the first and the second valve openings while suction is applied through one or both of the two working channels.

There is provided herein, according to an embodiment of the invention, a method of applying suction through at least one of two working channels of an endoscope, the method including a) installing a suction control unit on the endoscope, the suction control unit having a housing that further includes a first valve and a second valve on either side of a longitudinal axis of the housing, wherein a proximal end of the first and the second valve has respective first and second valve openings that lead through to a distal end of the first and the second valve, and wherein the distal end of the first and the second valve is aligned with first and second ports of the two working channels; a channel extending between the first and the second valve within the housing, wherein a channel axis is substantially perpendicular to the longitudinal axis of the housing; an opening extending from a front wall to a rear wall of the housing and through the channel between the first and the second valve; a switcher having a handle and a shaft extending from the handle along a long axis, wherein the shaft has a through hole such that a hole axis is substantially perpendicular to the long axis, and wherein the shaft is placed within the opening; b) generating suction using a pump connected to the endoscope; and c) manipulating the switcher between a first position and a second position, wherein in the first position the switcher opens the channel enabling suction to be applied through both the working channels while in the second position the switcher closes the channel enabling suction to be applied through one of the two working channels.

There is also provided herein, according to another embodiment of the invention, a method of applying suction through at least one of two working channels of an endoscope, the method including a) assembling a suction control unit by mounting a housing over first and second valves such that first and second receptacle tubes, formed on either side of a longitudinal axis of the housing, hold the first and second valves therein, wherein a proximal end of the first and second valves has first and second openings that lead through to a distal end, wherein a channel extends between the first and second receptacle tubes to enable fluid communication between the first and second valves such that a channel axis is substantially perpendicular to the longitudinal axis, and wherein an opening extends from a front wall to a rear wall of the housing and through the channel; placing a switcher in the opening, wherein the switcher has a handle and a shaft extending from the handle along a long axis, wherein the shaft has a plurality of pins and a through hole such that a hole axis is substantially perpendicular to the long axis, and wherein the shaft is held within the opening; b) installing the assembled suction control unit on the endoscope so that the distal end of the first and second valves is aligned with first and second ports of the two working channels; c) generating suction using a pump connected to the endoscope; and d) manipulating the switcher between a first position and a second position, wherein in the first position the switcher opens the channel enabling suction to be applied through both the working channels while in the second position the switcher closes the channel enabling suction to be applied through one of the two working channels.

In one embodiment, the suction control unit is fixedly installed on the endoscope while in another embodiment, the suction control unit is removably installed in the endoscope.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 4b is a perspective view of an assembled suction control unit with a valve switcher in a first position;

FIG. 4c is a perspective view of the assembled suction control unit with the valve switcher in a second position;

DETAILED DESCRIPTION OF THE INVENTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1A:
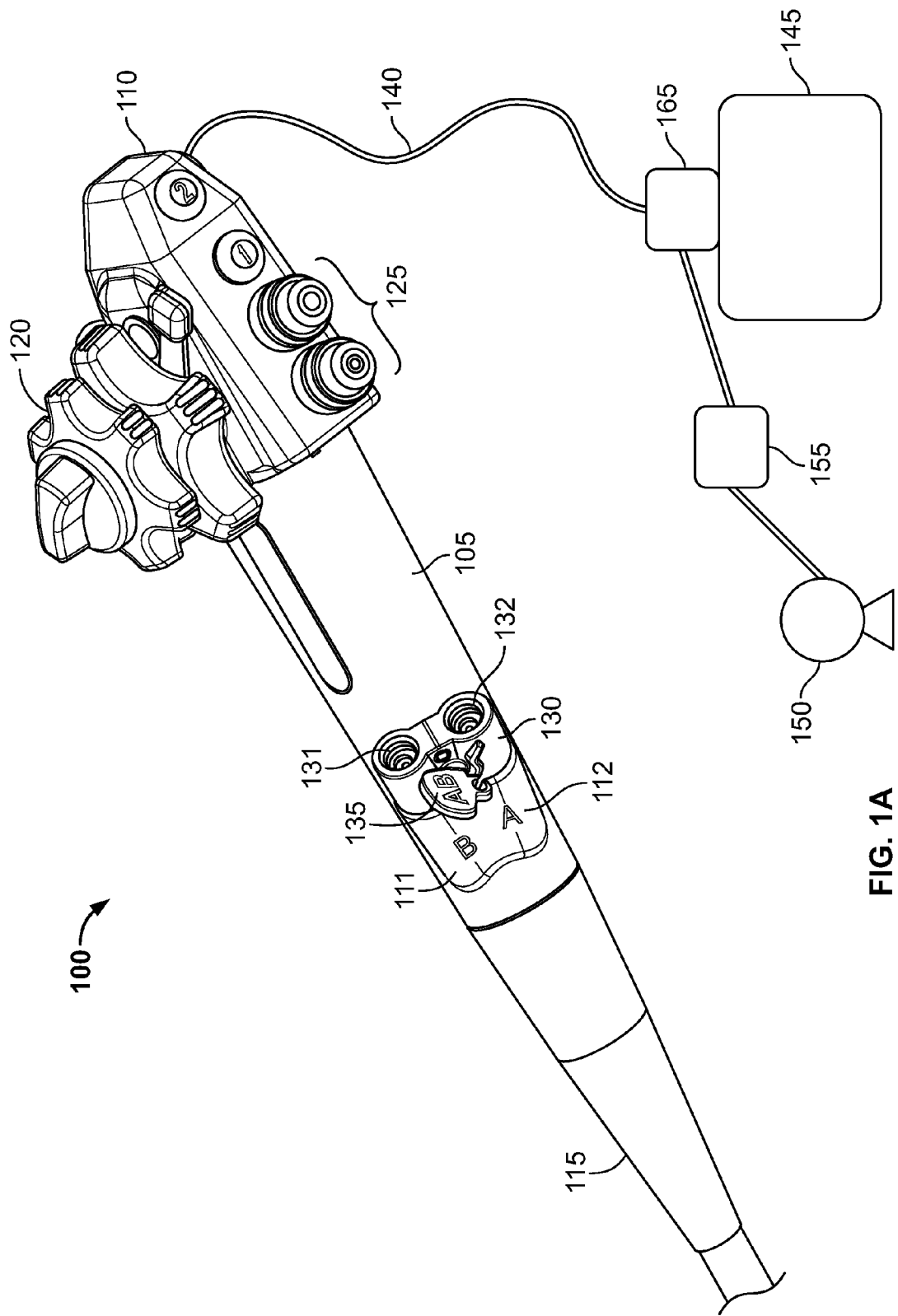
FIG. 1a is a pictorial view of an endoscopy system comprising a suction control unit of the present invention.
Figure 1B:
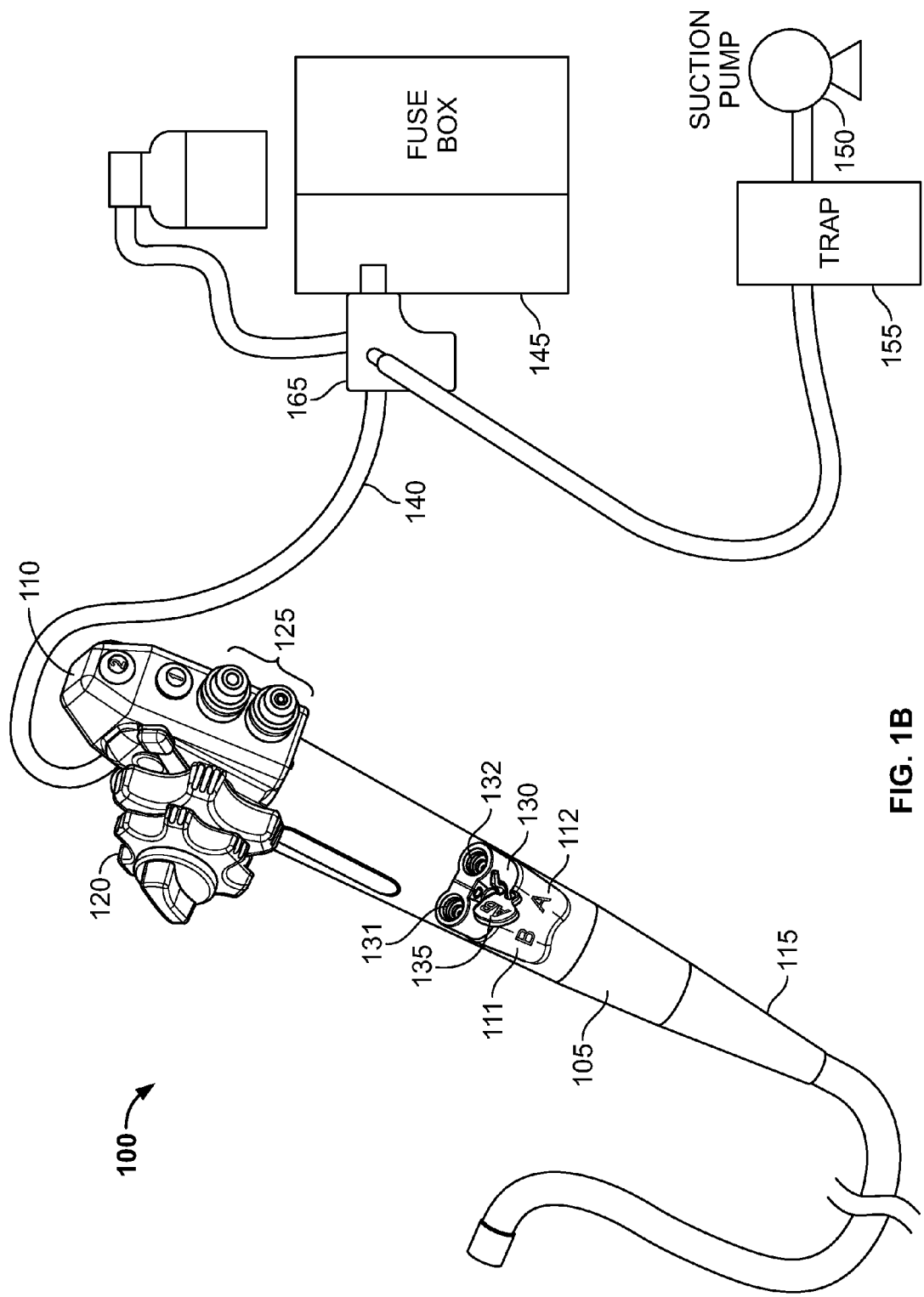
FIG. 1b is another pictorial view of an endoscopy system comprising a suction control unit of the present invention.

FIGS. 1a and 1b show pictorial views of an endoscopy system 100. System 100 comprises an endoscope 105 that, in accordance with an embodiment, is an endoscope with two service channels. The two service channels may both be located in the front of the endoscope as two front working channels as described in U.S. patent application Ser. No. 13/413,252, entitled "Multi Camera Endoscope Assembly Having Multiple Working Channels", filed on Mar. 6, 2012 and U.S. Provisional Patent Application No. 61/824,863, entitled "Multi-Viewing Element Endoscope Having Two Front Service Channels", and filed on May 17, 2013, and U.S. Provisional Patent Application No. 61/828,039, entitled "Multi-Viewing Element Endoscope Having Two Front Service Channels", and filed on May 28, 2013 by the present Applicant, and herein incorporated by reference. The two service channels may be located in the side of the endoscope as described in U.S. Provisional Patent Application No. 61/806,065, entitled "Multi Camera, Multi Jet Endoscope Having Two Side Service Channels", and filed on Mar. 28, 2013, and U.S. Provisional Patent Application No. 61/812,709, entitled "Multi Camera, Multi Jet Endoscope Having Two Side Service Channels", and filed on Apr. 16, 2013 by the present Applicant, and herein incorporated by reference. The two service channels may be referred to one front service channel and one or more side service channel as described in U.S. patent application Ser. No. 13/413,141, entitled "Multi-Camera Endoscope Having a Side Service Channel", filed on Mar. 6, 2012, which, in turn, relies upon U.S. Provisional Patent Application No. 61/449,743, of the same title, and filed on Mar. 7, 2011 by the present Applicant, and herein incorporated by reference.

Referring to FIGS. 1a and 1b simultaneously, the endoscope 105 comprises a handle 110, from which an insertion tube 115 emerges. Handle 110 is used to maneuver the insertion tube 115 within a body cavity with the use of operation knob(s) 120. The handle 110 also includes buttons/switches 125 which are used to control functions such as fluid injection and suction. The handle 110 further includes two working channel ports 111, 112, corresponding to the two service channels that run within the insertion tube 115 and open at a tip of the insertion tube 115. The opening of the service channels may be located at the front panel of the tip (not shown) and or at the tip side(s). The two working channel ports 111, 112 are used to insert surgical/treatment tools, and in one embodiment, apply suction therethrough.

In accordance with an embodiment, a suction control unit or module 130 of the present invention is removably or fixedly placed, mounted or attached on the endoscope 105 such that two valves 131, 132 of the suction unit 130 are aligned with the two working channel ports 111, 112. As a result surgical/treatment tools are now insertable into the two working channel ports 111, 112 via the two valves 131, 132. Similarly, suction can now be controlled or applied in one or both the working channel ports 111, 112 by selective use of the two valves 131, 132 (with or without the surgical/treatment tools in one or both working channels) using a valve switcher 135.

A utility cable 140 connects between the handle 110 and a main controller 145. Utility cable 140 may include therein one or more fluid channels and one or more electrical channels. A suction pump 150 outside the endoscope is used to apply negative pressure. When the suction pump 150 is switched on (using one of the buttons/switches 125), suction is initiated in the body cavity through one or both of the working channels 111, 112 (by selective use of valve switcher 135), a suction tube through a connector to a trap 155 outside the endoscope 105. In one embodiment, when the physician presses a button (shown as buttons/switches 125) on the endoscope, suction is applied from the suction pump 150. In one embodiment, the suction pump 150 is connected to the scope 105 through a main connector 165 into the utility cable 140, through the handle 110 and into the insertion tube 115 and all the way back. Typically, the trap 155 is placed between the main connector 165 and the suction pump 150. The sucked object travels inside two of the working channels 111, 112, into the handle 110. In one embodiment, suction can be applied on both the service channels 111, 112, however the two channels are combined inside the handle 110 into one due to space limitations.

Figure 2A:
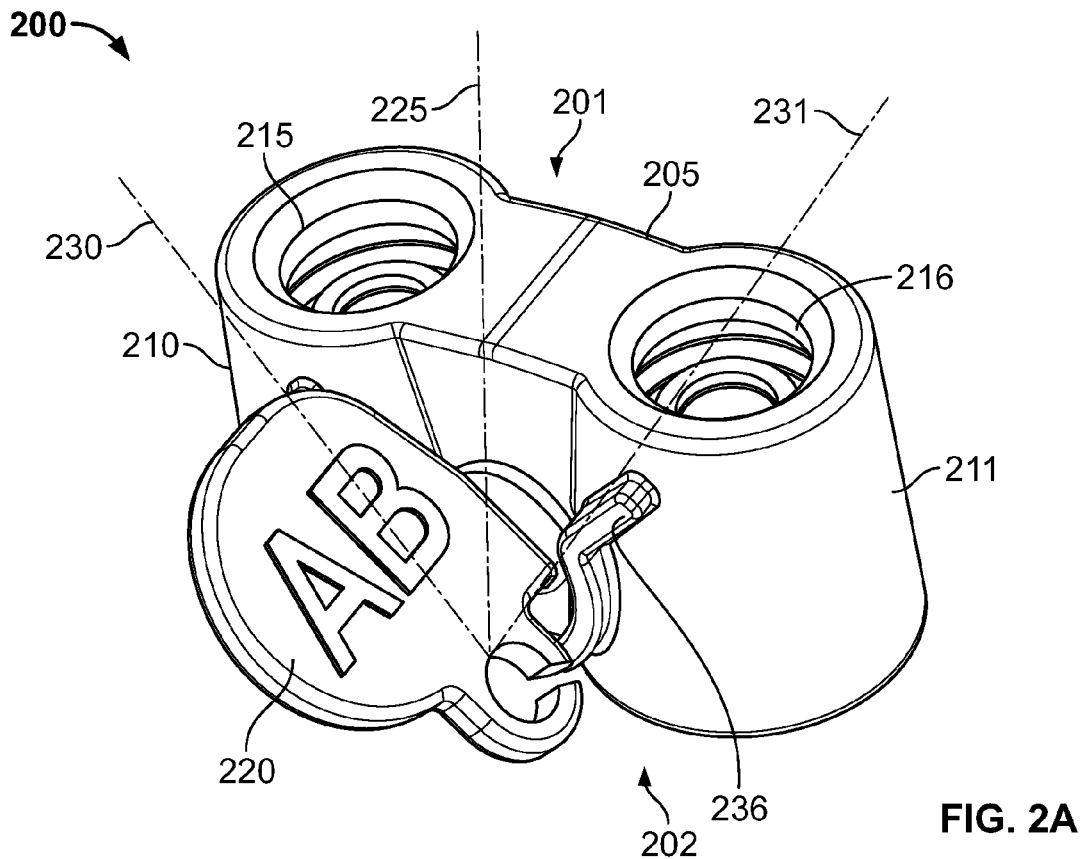
FIG. 2a is a perspective view of the suction control unit with a valve switcher in a first position.
Figure 2B:
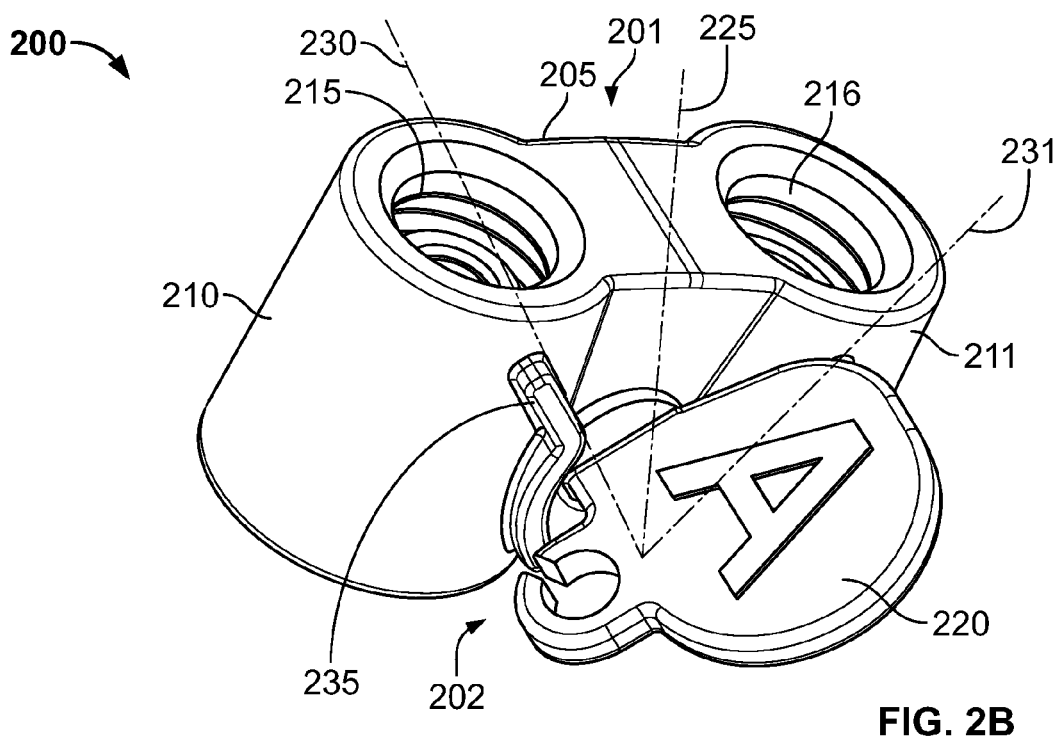
FIG. 2b is a perspective view of the suction control unit with the valve switcher in a second position.

FIGS. 2a and 2b show perspective views of the suction control unit or module 200 in accordance with an embodiment of the present invention. The suction control unit 200 comprises a housing 205 that includes dual (two) suction valves 210, 211 formed on either side of a longitudinal axis 225 of the suction control unit 200. A proximal end 201 of the suction valves 210, 211 includes two corresponding valve openings 215, 216 that lead through to a distal end 202 of the suction valves 210, 211. The distal end 202 of the suction valves 210, 211 is placed on two working channel ports (shown as 111, 112 in FIG. 1) such that the suction valves 210, 211 (and the corresponding valve openings 215, 216) align with the two working channel ports, as described with reference to FIG. 1. A valve switcher 220 can be turned to enable or allow for suction from one or both of the two suction valves 210, 211.

In one embodiment, the valve switcher 220 can be turned/rotated about 45 degrees on either side of the longitudinal axis 225. When the valve switcher 220 is turned/rotated to be in a first position 230, as shown in FIG. 2a, it causes an internal channel between the dual suction valves 210, 211 to open resulting in suction to be applied to both the valves 210, 211 and therefore to both corresponding working channels or ports. When the valve switcher 220 is turned/rotated to be in a second position 231, as shown in FIG. 2b, it causes the internal channel between the dual suction valves 210, 211 to close resulting in suction to be applied to only one of the two valves 210, 211 and therefore to only one out of the two corresponding working channels or ports. Switcher tracks 235, 236 function as stoppers or limiters such that in the first position 230 the valve switcher 220 rests against the track 235 while in the second position 231 the valve switcher 220 rests against the track 236. Thus, the tracks 235, 236 restrict, stop or limit the rotation of the valve switcher 220 beyond the tracks 235, 236.

A physician can control the amount of suction to be applied during an endoscopic procedure by enabling or allowing suction to be applied to one or both of the working channels. The suction can be applied with a surgical/treatment tool in one or both the working channels or without a surgical tool in any of the two working channels.

Figure 3A:
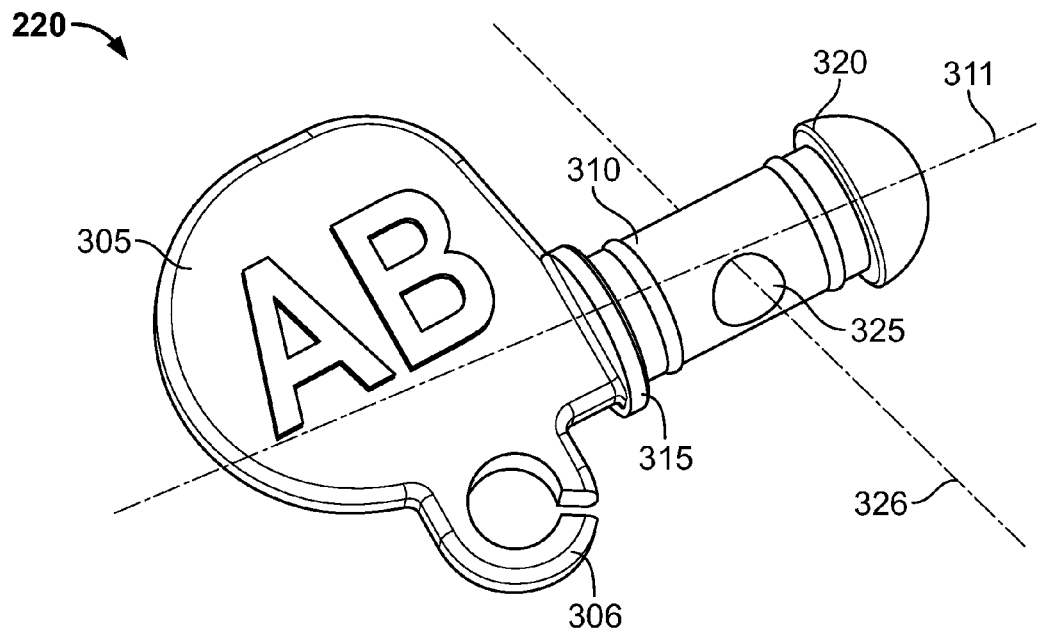
FIG. 3a is a perspective view of the valve switcher.

As shown in FIG. 3a, the valve switcher 220 comprises a switcher handle 305 from which emerges a cylindrical shaft 310. The shaft 310 has a first surface 315 at one end (close to or proximate to the switcher handle 305) and a second surface 320 at the other end. In one embodiment, the diameter of the shaft 310 is $D_1$ while that of the first and second surfaces 315, 320 is $D_2$. In one embodiment, $D_1$ is less than $D_2$. In one embodiment, the first surface 315 is ring shaped while the second surface 320 has a semi-spherical shape. A through hole 325 is formed on the shaft 310 such that a hole axis 326 of the hole 325 is substantially perpendicular to the long axis 311 of the shaft 310. The through hole 325 controls the opening or closing of the internal channel between the dual suction valves 210, 211 (of FIGS. 2a, 2b). In one embodiment, the switcher handle 305 has an open ring 306 at one end. As shown in FIG. 3c the open ring 306 is used to loosely host two stoppers/plugs 330 configured for the two valve openings 215, 216 of the suction unit 200.

Figure 3B:
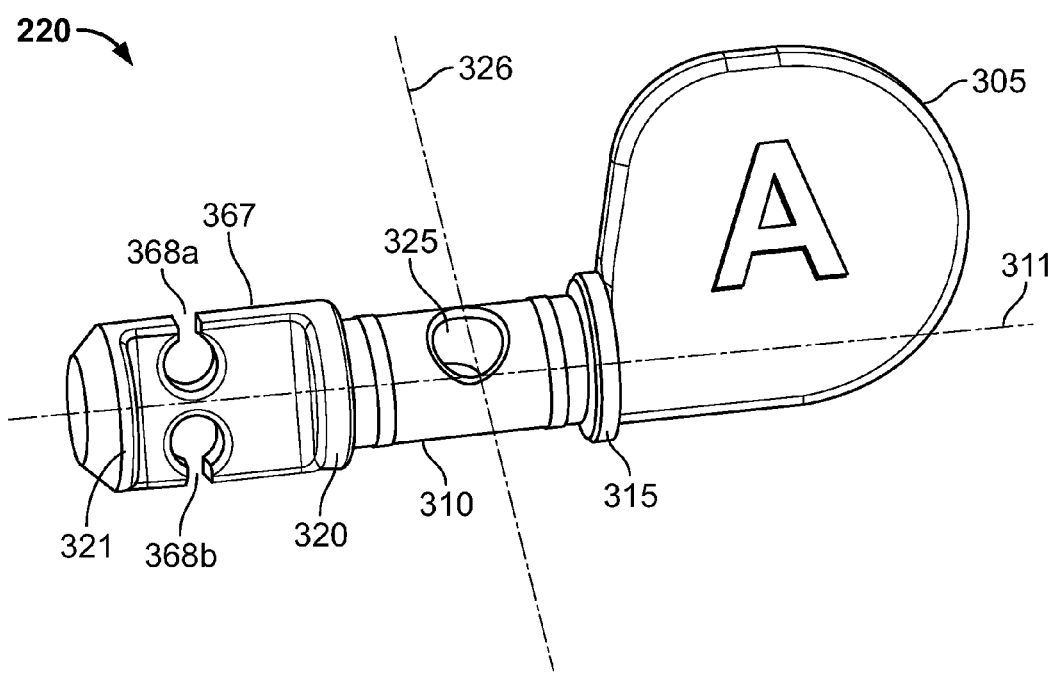
FIG. 3b is a perspective view of another embodiment of the valve switcher.
Figure 3C:
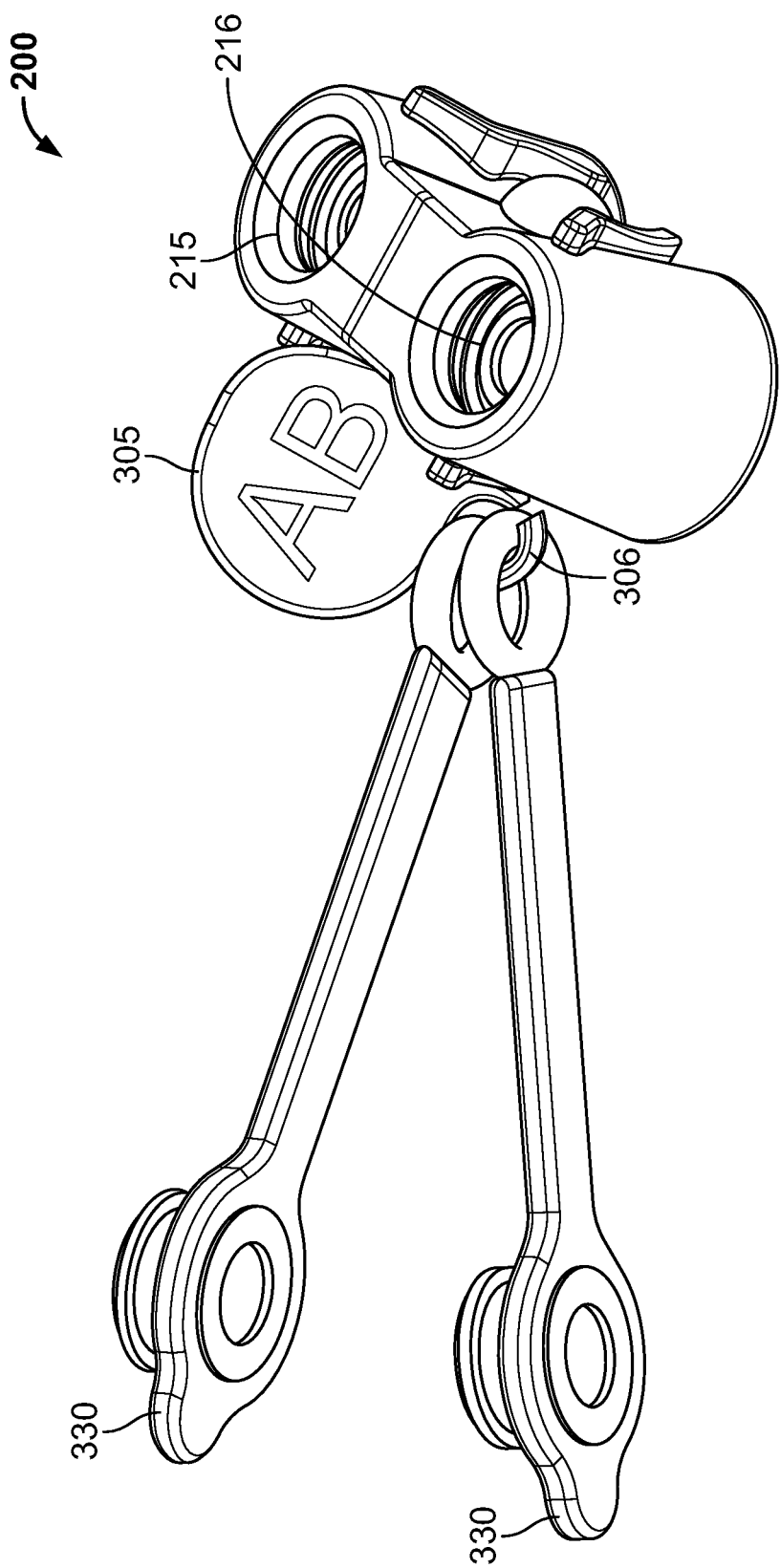
FIG. 3c is a perspective view of the suction control unit showing two stoppers/plugs held in an open ring of the valve switcher.
Figure 3D:
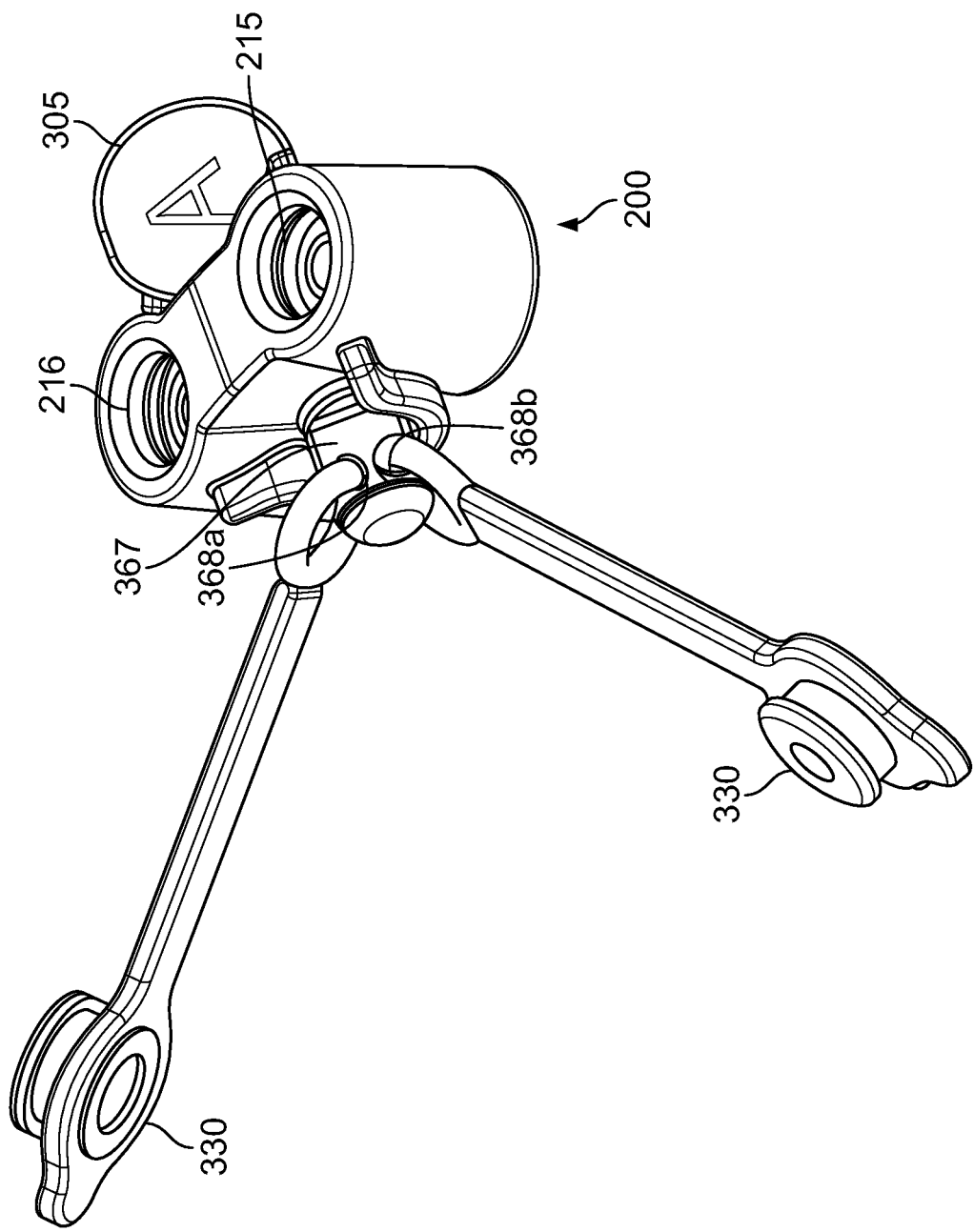
FIG. 3d is a perspective view of the suction control unit showing the two stoppers/plugs held in an open ring of the valve switcher, according to one embodiment of the present invention.

As shown in FIG. 3b, another embodiment of the valve switcher 220 comprises a switcher handle 305 from which emerges a cylindrical shaft 310. The shaft 310 has a first surface 315 at one end and a second surface 320 at the other end. In one embodiment, the diameter of the shaft 310 is $D_1$ while that of the first and second surfaces 315, 320 is $D_2$. In one embodiment, $D_1$ is less than $D_2$. In one embodiment, the first and second surfaces 315, 320 are ring-shaped. A through-hole 325 is formed on the shaft 310 such that the axis 326 of the hole 325 is perpendicular to the long axis 311 of the shaft 310. The through hole 325 controls the opening or closing of the internal channel between the dual suction valves 210, 211 (of FIGS. 2a, 2b). In one embodiment, the second surface 320 has a cylindrical or rectangular extension 367 (along the long axis 311) which has two open rings 368a and 368b formed on opposite long sides (that is, the sides that are parallel to the long axis 311) of the cylindrical or rectangular extension 367. Extension 367 ends with an end surface 321. In one embodiment, the end surface 321 has a ring shape and has a diameter of $D_2$. As shown in FIG. 3d the two open rings 368a and 368b are used to host two stoppers/plugs 330 configured for the two valve openings 215, 216 of the suction unit 200.

Figure 2C:
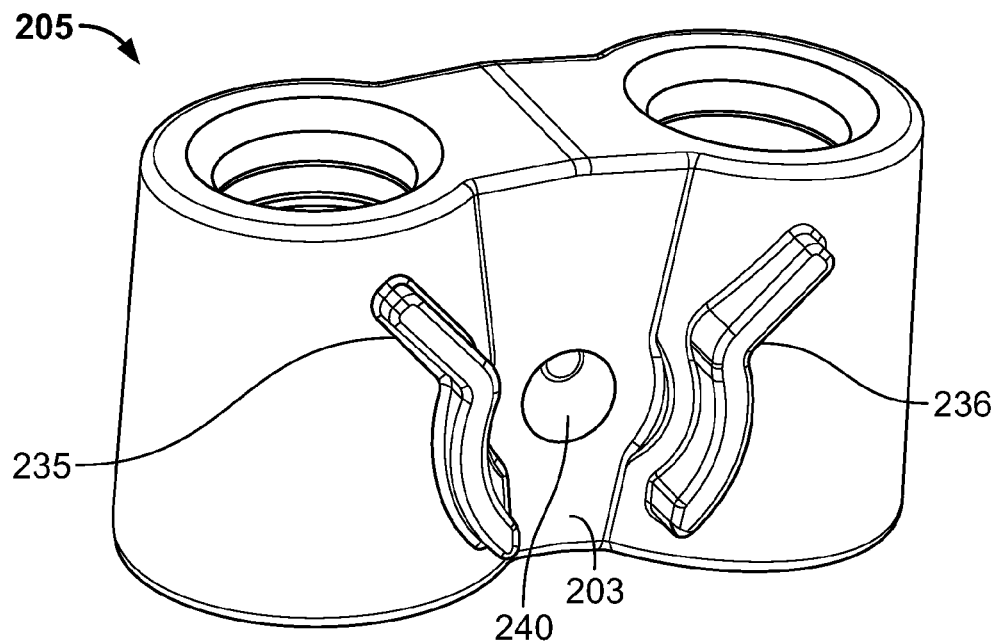
FIG. 2c is a front view of housing of the suction control unit without the valve switcher.
Figure 2D:
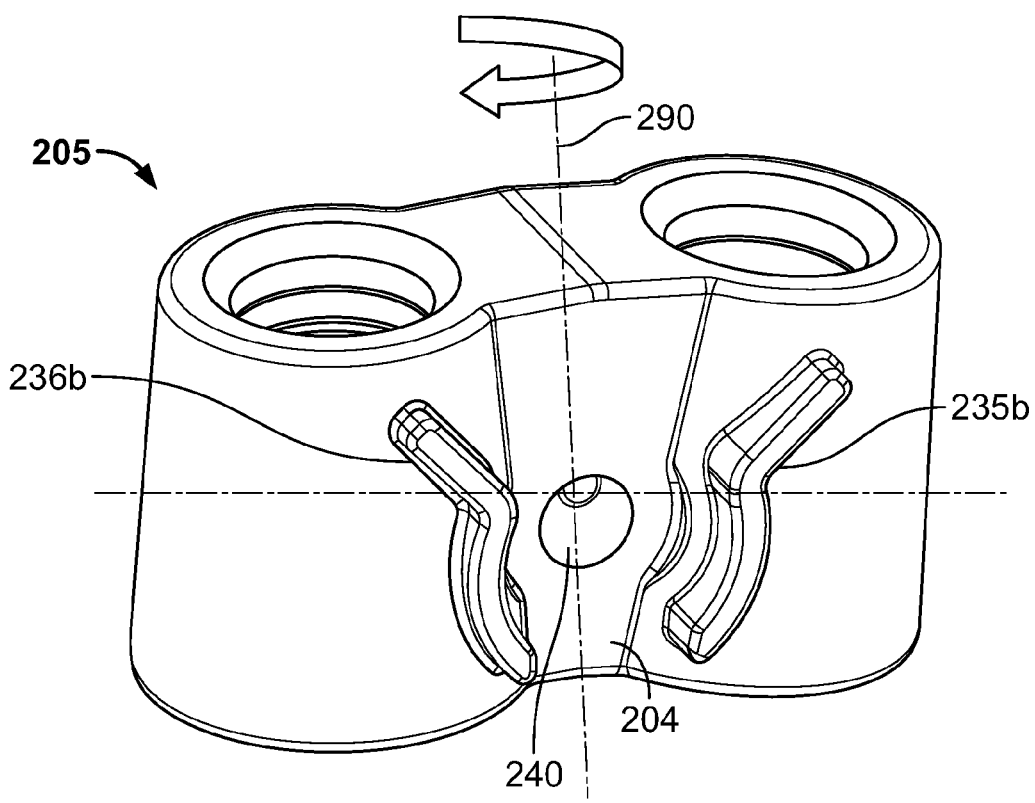
FIG. 2d is a rear view of the housing of the suction control unit without the valve switcher.

FIGS. 2c and 2d are front and rear perspective views, respectively, of the housing 205 of the suction control unit 200. As shown in FIG. 2c, a switcher through opening 240 crosses the housing 205 from a front wall 203 to a rear wall 204 and is adapted to hold the valve switcher 220 of FIG. 3a or 3b. Referring now to FIGS. 2c, 2d, 3a and 3b simultaneously, the internal diameter of the switcher opening 240 is $D_1$ which is the same as the diameter $D_1$ of the shaft 310.

When the valve switcher (220 of FIG. 3a or 3b) is located within the switcher opening 240, the first surface 315 abuts against the front wall 203 of the housing 205 while the second surface 320 protrudes from and abuts against the rear wall 204 of the housing 205 (as shown in FIG. 2d). Since the diameter $D_2$ of the first and second surfaces 315, 320 is greater than the internal diameter $D_1$ of the switcher opening 240, the valve switcher 220 is securely held within the opening 240 without any lateral movement of the valve switcher 220 along the long axis 311 of the shaft 310. It may be noted that the housing 205 has an axis of symmetry 290, as shown in FIG. 2d. Therefore in one embodiment, (referring to FIGS. 2c and 2d), the valve switcher may be inserted inside switcher opening 240 through front wall 203 or rear wall 204. In one embodiment, switcher tracks 235, 236 and 236b, 235b are located on both sides 203 and 204 respectively, of the housing 205.

Figure 2E:
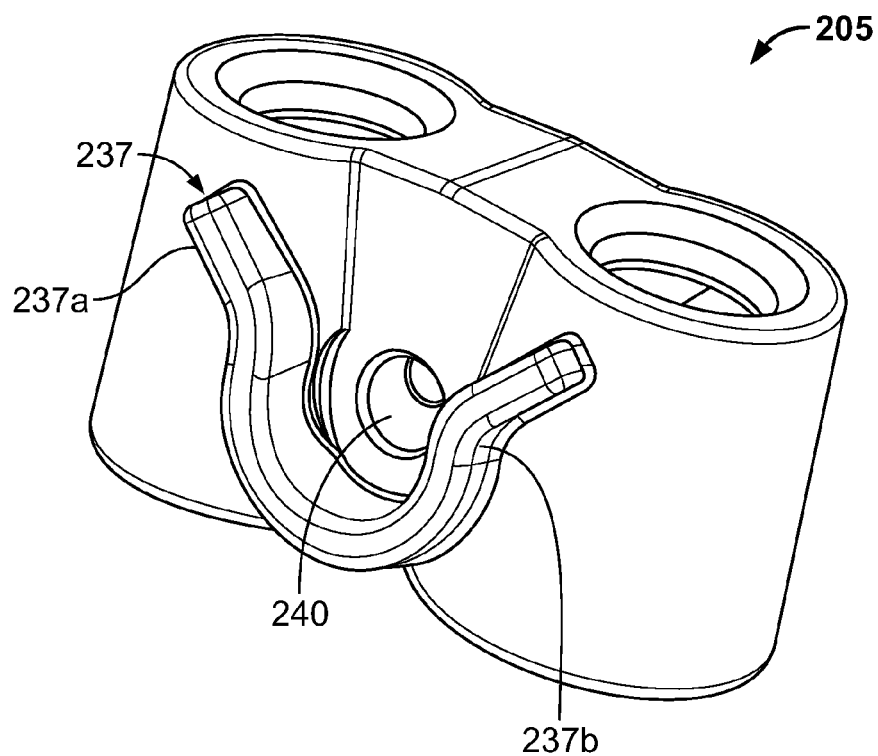
FIG. 2e is a front view of another embodiment of the housing of the suction control unit without the valve switcher, where the switcher track is a single, continuous unit.

FIG. 2e is a perspective view of another embodiment of the housing 205 of the suction control unit 200. Here, the switcher track 237 is designed as a single, continuous unit, instead of two separate switcher tracks as shown in the embodiments of FIGS. 2c and 2d. Switcher track 237 functions as stopper or limiter such that in the first position 230 (indicated in FIG. 2a) the valve switcher 220 rests against the track 237 on the side wall 237a while in the second position 231 (indicated in FIG. 2b) the valve switcher 220 rests against the second side wall 237b of track 237. Thus, the track 237 restricts, stops or limits the rotation of the valve switcher 220 beyond the tracks walls 237a, 237b. It may be appreciated that having a single switcher track reduces ambiguity and enables the user to correctly insert the valve switcher into the housing.

Figure 2F:
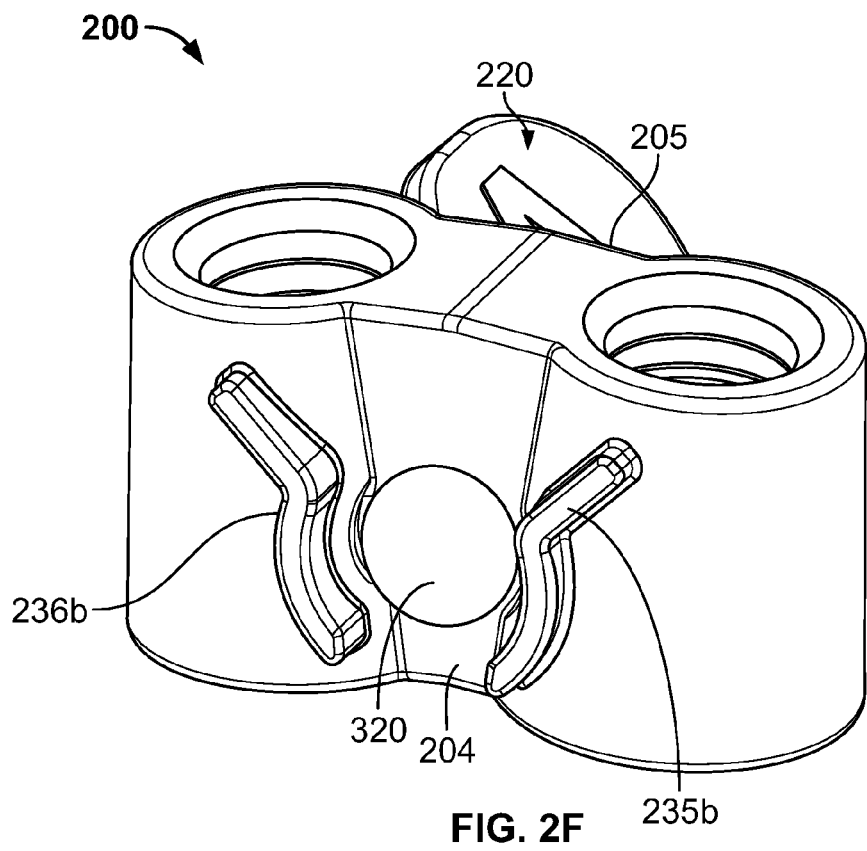
FIG. 2f is a rear view of the suction control unit with the valve switcher.

FIG. 2f is a rear view of the suction control unit 200 with the valve switcher 220 coupled to it. Referring to FIG. 2f, switcher tracks 236b, 235b are provided against the rear wall 204 of the housing 205 of the suction control unit. Since the valve switcher 220 is coupled to the suction control unit, the semi-spherical end surface 320 of the cylindrical shaft of the valve switcher (shown as 310 in FIG. 3a), can be seen on the rear wall 204 of the housing.

Figure 2G:
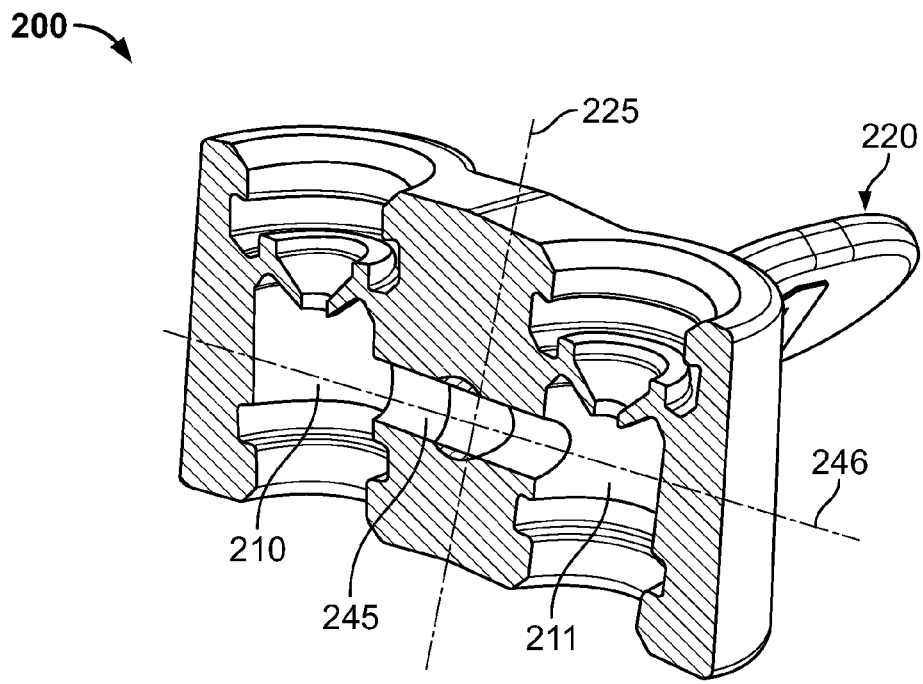
FIG. 2g is a rear side cross-sectional view of the suction control unit with the valve switcher in the first position.
Figure 2H:
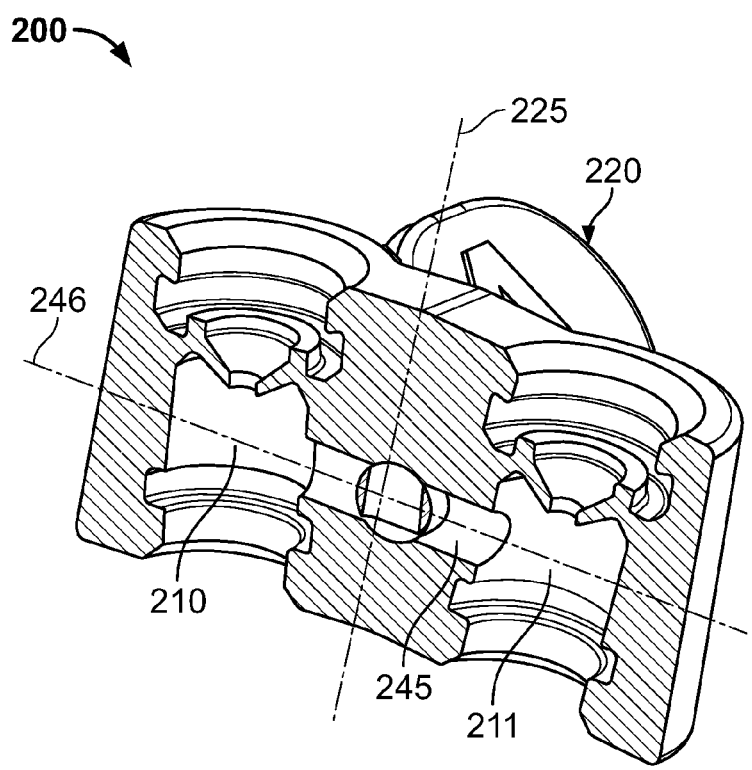
FIG. 2h is a rear side cross-sectional view of the suction control unit with the valve switcher in the second position.

FIGS. 2g and 2h are cross-sectional rear-side views of the suction control unit 200 showing the internal channel 245 between the dual suction valves 210, 211. In one embodiment, a channel axis 246 of the internal channel 245 is substantially perpendicular to the longitudinal axis 225 of the unit 200.

Reference will now be made to FIGS. 2c, 2e, 2g, 2h 3a and 3b simultaneously. The switcher opening 240 that crosses the housing 205 from one side to the other also runs through the internal channel 245. When the valve switcher 220 is turned/rotated to be in the first position of FIG. 2g, it causes the through hole 325 (on the switcher shaft 310) to align with the internal channel 245 such that the hole axis 326 is substantially parallel to and approximately coincides with the axis 246 of the internal channel 245. In other words, the internal channel 245 is now open enabling communication between the dual suction valves 210, 211 via the hole 325. This opening of the internal channel 245 allows suction to be applied to both valves 210, 211 and therefore to corresponding working channels or ports. When the valve switcher 220 is turned/rotated to be in the second position of FIG. 2h, it causes the through-hole 325 (on the switcher shaft 310) to misalign with the internal channel 245 such that the hole axis 326 is now substantially perpendicular to the axis 246 of the internal channel 245. In other words, the internal channel 245 is now closed restricting communication between the dual suction valves 210, 211 via the hole 325. This closing of the internal channel 245 allows suction to be applied to only one of the two valves 210, 211 and therefore to only one of the two corresponding working channels or ports.

As discussed earlier, the valve switcher 220 can be turned/rotated about 45 degrees on either side of the longitudinal axis 225 of the unit 200, in one embodiment. This means that, in one embodiment, the total angular rotation or turn of the valve switcher 220 is 90 degrees. Thus, while in the first position of FIG. 2g the hole axis 326 is parallel to and approximately coinciding with the axis 246 of the internal channel 245; in the second position of FIG. 2h, which is 90 degrees rotated from the first position 230, the hole axis 326 is perpendicular to the axis 246 of the internal channel 245. Persons of ordinary skill in the art should note that the angular turn or rotation of the valve switcher 220 of 45 degrees, on either side of the longitudinal axis 225 of the unit 200, is only exemplary and could be different in alternate embodiments provided the switching from the first position to the second position and vice versa causes the through hole 325 to close or open the internal channel 245 for suction to be applied to any one or both of the dual suction valves 210, 211.

Figure 4A:
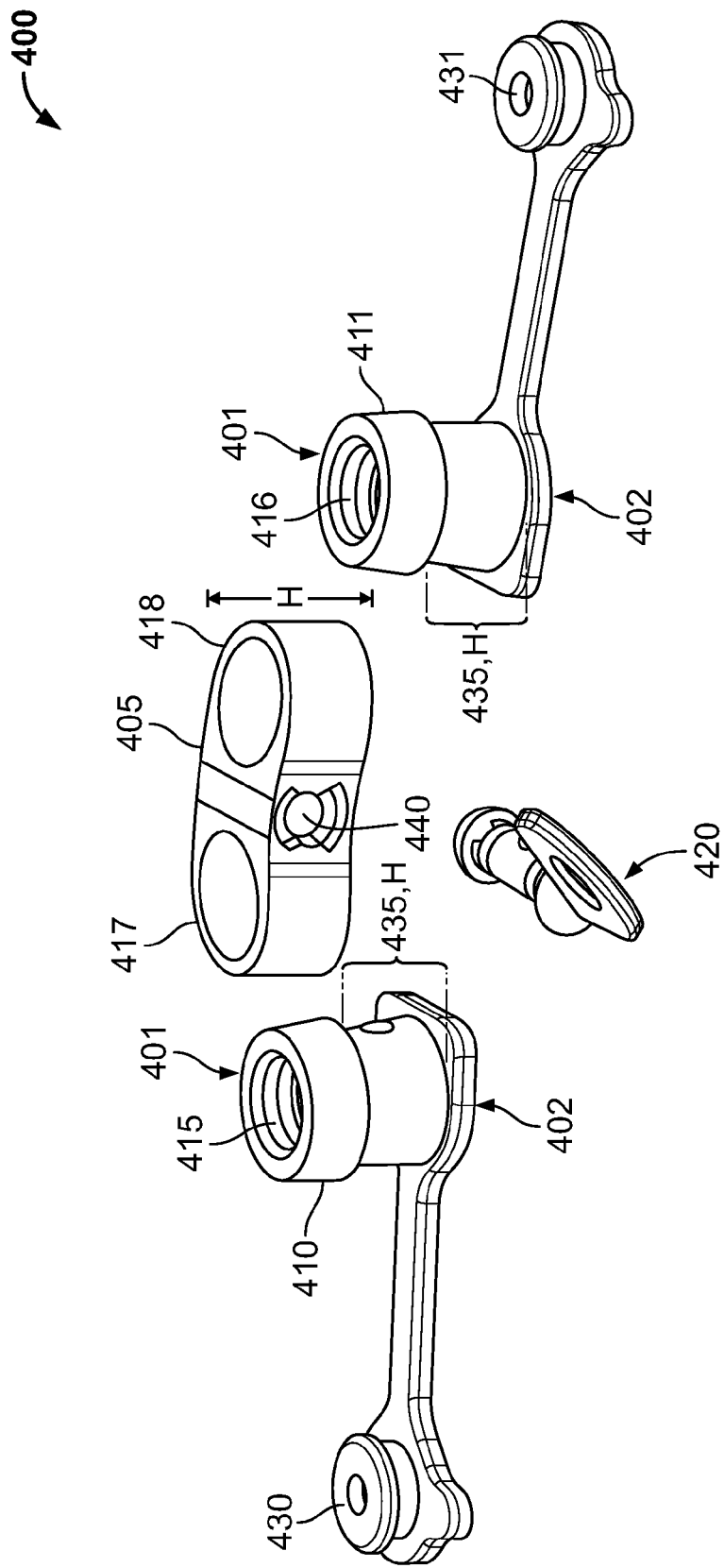
FIG. 4a is a disassembled view of a plurality of components of a suction control unit in accordance with another embodiment of the present specification.

FIG. 4a is a disassembled view of a plurality of components of a suction control unit or module 400 in accordance with another embodiment of the present invention, while FIGS. 4b and 4c are assembled perspective views of the suction control unit 400. It should be noted herein that the embodiment shown in FIG. 4a, having discrete components, improve the manufacturability of the suction control unit and/or enable it to be reprocessed. The plurality of components can be factory assembled for ready-to-use deployment or can be assembled and/or disassembled on-site by a caregiver. Referring simultaneously to FIGS. 4a through 4c, the suction control unit 400 comprises a dual valve body or housing 405, first and second suction valves 410, 411 retaining first and second stoppers/plugs 430, 431 at a distal end 402, and a valve switcher 420. The dual valve body or housing 405 has first and second receptacle tubes 417, 418 to hold or encompass corresponding first and second suction valves 410, 411. A switcher through opening 440 crosses the dual valve body or housing 405 from one side to the other and is adapted to hold the valve switcher 420. A proximal end 401 of the suction valves 410, 411 includes two corresponding valve openings 415, 416 that lead through to the distal end 402 of the suction valves 410, 411. In accordance with an embodiment, the distal end 402 of the first and second suction valves 410, 411 firmly hold or retain first and second stoppers/plugs 430, 431 configured for the two valve openings 415, 416. The distal end 402 of the suction valves 410, 411 is placed on two working channel ports (shown as 111, 112 in FIG. 1) such that the suction valves 410, 411 (and the corresponding valve openings 415, 416) align with the two working channel ports, as has been described with reference to FIG. 1.

In one embodiment, the suction valves 410, 411 comprise a depression or groove 435 of height 'H' corresponding to height 'H' of the first and second receptacle tubes 417, 418. When assembled, as shown in FIGS. 4b and 4c, the first and second suction valves 410, 411 are fitted into and held within the corresponding first and second receptacle tubes 417, 418 such that the first and second receptacle tubes 417, 418 snugly fit into the depression or groove 435. In one embodiment, the depth 'd' of the depression or groove 435 is equal to the thickness 't' of the walls of the first and second receptacle tubes 417, 418 so that when assembled the outer walls of the receptacle tubes 417, 418 lie flush with the outer walls of the suction valves 410, 411.

The valve switcher 420 can be turned to enable or allow for suction from one or both of the two suction valves 410, 411. In one embodiment, the valve switcher 420 can be turned/rotated about 45 degrees on either side of a longitudinal axis 425 of the suction control unit 400. When the valve switcher 420 is turned/rotated to be in a first position 445, as shown in FIG. 4b, it causes an internal channel between the dual suction valves 410, 411 to close resulting in suction to be applied to only one of the two valves 410, 411 and therefore to only one out of the two corresponding working channels or ports. When the valve switcher 420 is turned/rotated to be in a second position 446, as shown in FIG. 4c, it causes the internal channel between the dual suction valves 410, 411 to open resulting in suction to be applied to both the valves 410, 411 and therefore to both corresponding working channels or ports. When required, the stoppers/plugs 430, 431 can be folded upwards to fit into and thereby close one or both of the two valve openings 415, 416 as shown in FIGS. 4h and 4i where the valve switcher 420 is in the first and second position respectively.

A physician can control the amount of suction to be applied during an endoscopic procedure by enabling or allowing suction to be applied to one, both or neither of the working channels. The suction can be applied with a surgical/treatment tool in one or both the working channels or without a surgical tool in any of the two working channels.

Figure 5:
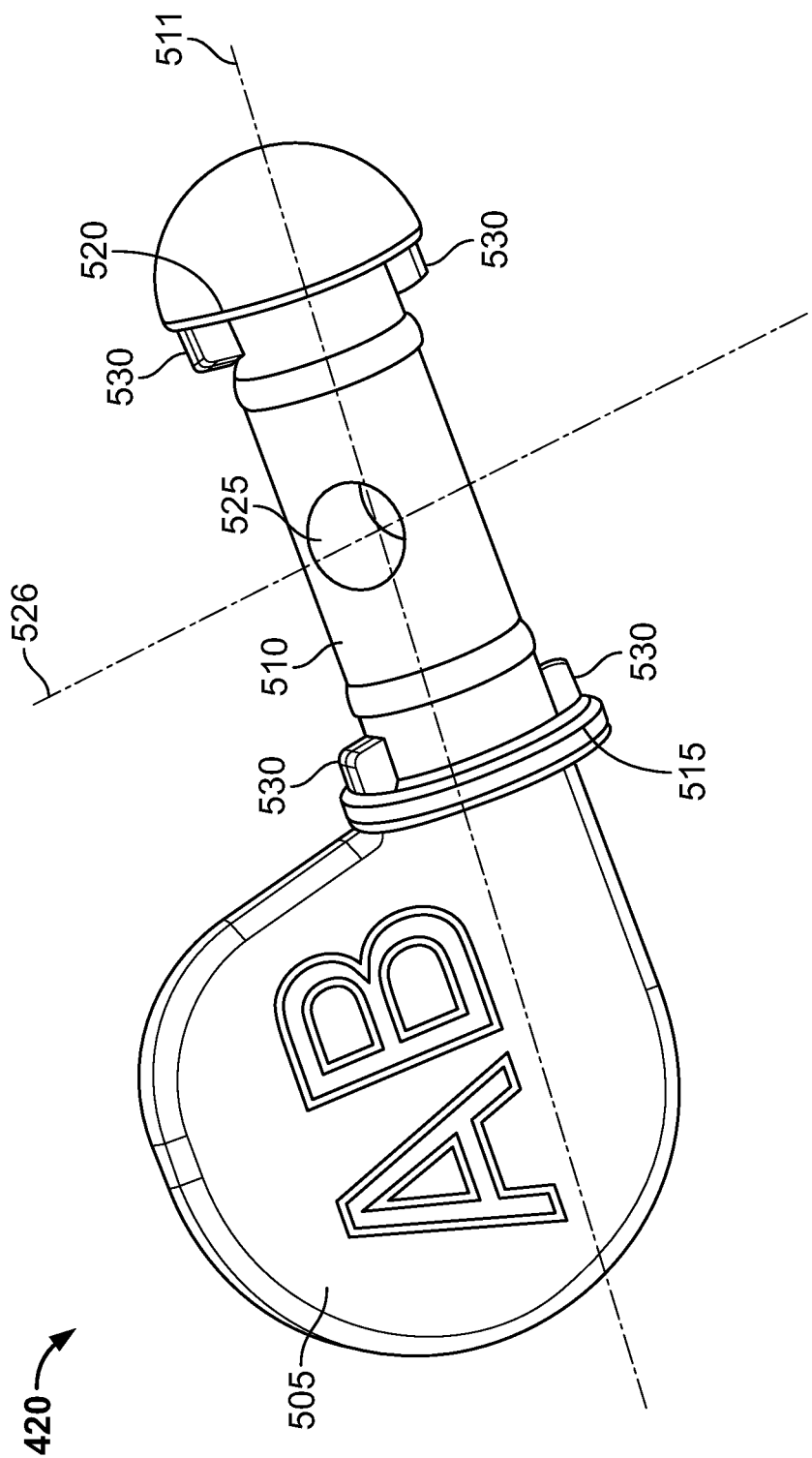
FIG. 5 is a perspective view of an embodiment of the valve switcher.

As shown in FIG. 5, the valve switcher 420 comprises a switcher handle 505 from which emerges a cylindrical shaft 510. The shaft 510 has a first surface 515 at one end (close to or proximate to the switcher handle 505) and a second surface 520 at the other end. In one embodiment, the diameter of the shaft 510 is $D_1$ while that of the first and second surfaces 515, 520 is $D_2$. In one embodiment, $D_1$ is less than $D_2$. In one embodiment, the first surface 515 is ring shaped while the second surface 520 has a semi spherical shape. A plurality of pins 530, which in one embodiment is four, are formed on the shaft 510 abutting the first and second surfaces 515, 520. A through-hole 525 is formed on the shaft 510 such that a hole axis 526 of the through-hole 525 is substantially perpendicular to the long axis 511 of the shaft 510. The through-hole 525 controls the opening or closing of the internal channel between the dual suction valves 410, 411 of FIGS. 4b and 4c.

Figure 4D:
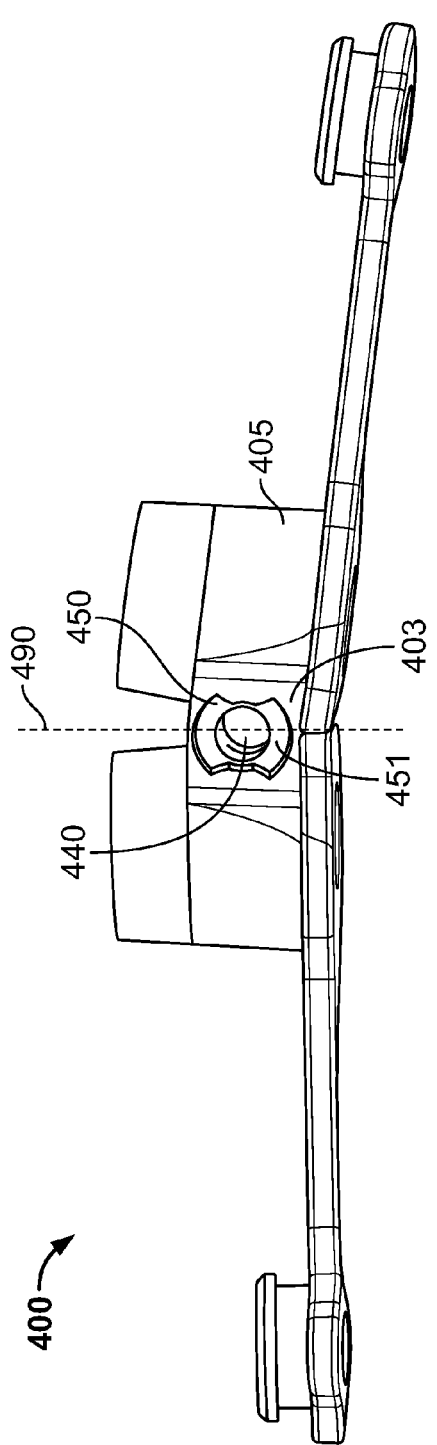
FIG. 4d is a front view of the assembled suction control unit without the valve switcher.
Figure 4E:
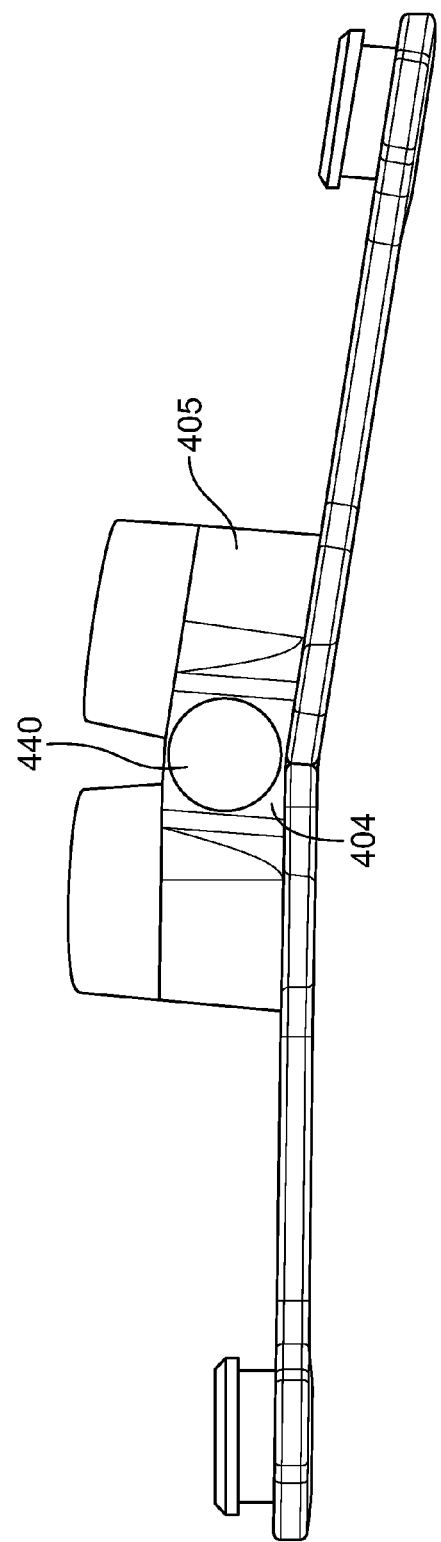
FIG. 4e is a rear view of the assembled suction control unit without the valve switcher.

FIGS. 4d and 4e are front and rear perspective views, respectively, of the suction control unit 400. As shown in FIG. 4d, the switcher through opening 440 crosses the dual valve body 405 from a front wall 403 to the rear wall 404 and is adapted to hold the valve switcher 420 of FIG. 5. Referring now to FIGS. 4b through 4e and 5 simultaneously, the switcher through opening 440 has upper and lower switcher tracks 450, 451 that engage or align with the pins 530 of the valve switcher 420 to thereby restrict, stop or limit the rotational motion of the valve switcher 420 to the first and second positions 445, 446. In one embodiment, the upper and lower switcher tracks 450, 451 are formed only on the front wall 403 whereas in another embodiment, the upper and lower switcher tracks 450, 451 are formed on both the front wall 403 and the rear wall 404 of the dual valve body 405.

The internal diameter of the switcher opening 440 is $D_1$ which is the same as the diameter $D_1$ of the shaft 510. When the valve switcher 420 is located within the switcher opening 440, the first surface 515 abuts against the front wall 403 of the dual valve body 405 while the second surface 520 protrudes from and abuts against the rear wall 404 of the dual valve body 405 (as shown in FIG. 4e). Since the diameter $D_2$ of the first and second surfaces 515, 520 is greater than the internal diameter $D_1$ of the switcher opening 440, the valve switcher 420 is securely held within the opening 440 without any lateral movement of the valve switcher 420 along the long axis 511 of the shaft 510. It may be noted that the dual valve body 405 has an axis of symmetry 490, as shown in FIG. 4d. Therefore in one embodiment (where the upper and lower switcher tracks 450, 451 are formed on both front and rear walls 403, 404 of the dual valve body 405), the valve switcher 420 may be inserted inside switcher opening 440 through front wall 403 or rear wall 404.

Figure 4F:
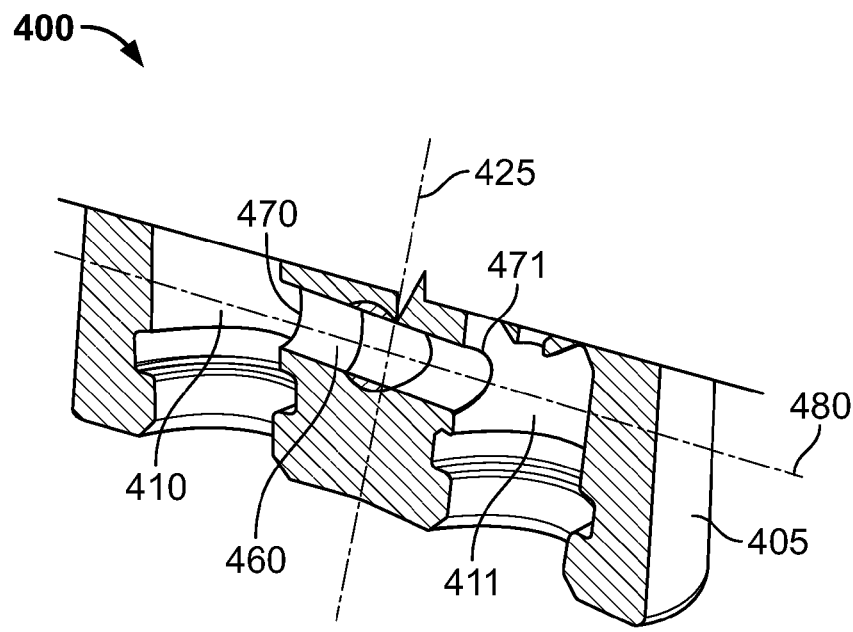
FIG. 4f is a rear side cross-sectional view of a dual valve body of the suction control unit with the valve switcher in the first position.
Figure 4G:
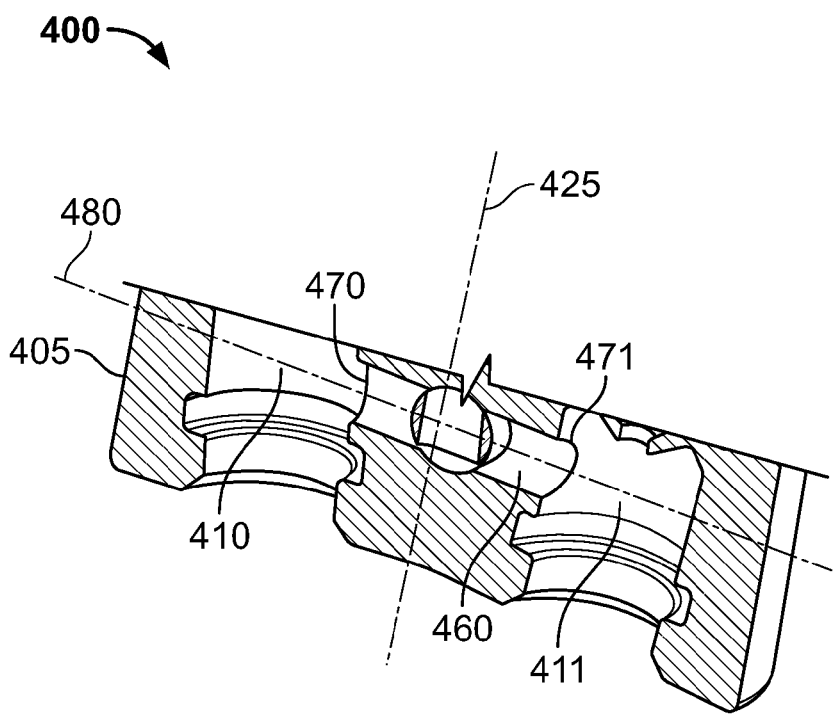
FIG. 4g is a rear side cross-sectional view of the dual valve body of the suction control unit with the valve switcher in the second position.
Figure 4H:
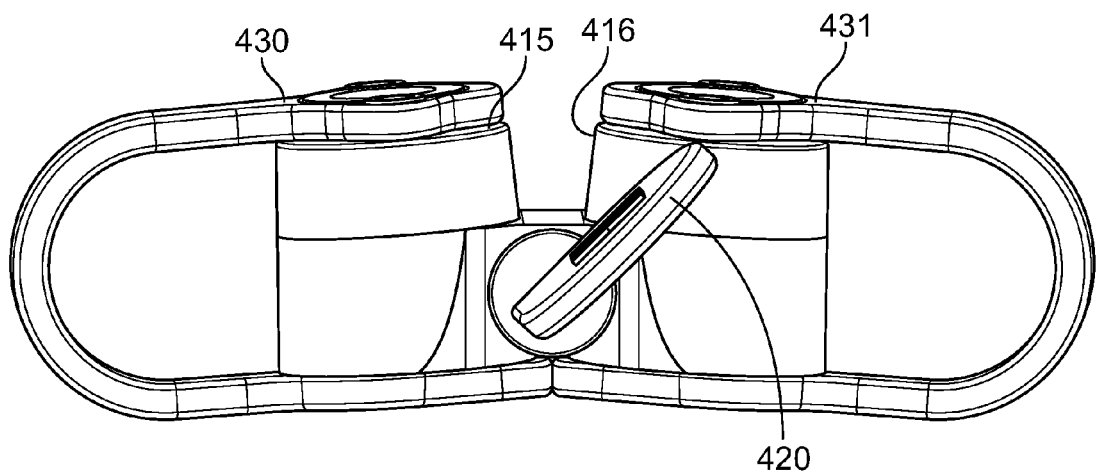
FIG. 4h is a perspective view of the assembled suction control unit with stoppers/plugs closing first and second valve openings while the valve switcher is in the first position.
Figure 4I:
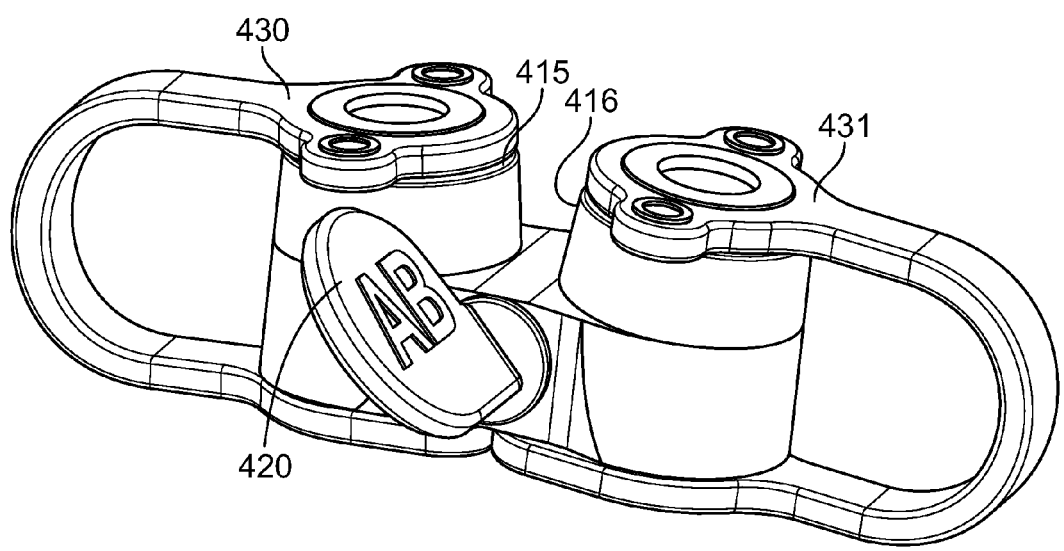
FIG. 4i is a perspective view of the assembled suction control unit with stoppers/plugs closing first and second valve openings while the valve switcher is in the second position.

FIGS. 4f and 4g are cross-sectional rear-side views of the dual valve body 405. The dual valve body 405 has an internal channel 460 and openings 470, 471 that align with corresponding holes in suction valves 410, 411 when the dual valve body 405 is mounted over or assembled with the suction valves 410, 411 (as shown in FIGS. 4b and 4c) thereby enabling fluid communication between the suction valves 410, 411 held within the first and second receptacle tubes 417, 418 (FIG. 4a). In one embodiment, the channel axis 480 of the internal channel 460 is substantially perpendicular to the longitudinal axis 425 of the unit 400.

Reference will now be made to FIGS. 4d, 4f, 4g and 5 simultaneously. The switcher opening 440 that crosses the dual valve body 405 from the front wall 403 to the rear wall 404 also runs through the internal channel 460. When the valve switcher 420 is turned/rotated to be in the first position of FIG. 4f, it causes the through hole 525 (on the switcher shaft 510) to align with the internal channel 460 such that the hole axis 526 is substantially parallel to and approximately coincides with the channel axis 480 of the internal channel 460. In other words, the internal channel 460 is now open enabling communication between the dual suction valves 410, 411 via the hole 525. This opening of the internal channel 460 allows suction to be applied to both valves 410, 411 and therefore to corresponding both working channels or ports. When the valve switcher 420 is turned/rotated to be in the second position of FIG. 4g, it causes the through-hole 525 (on the switcher shaft 510) to misalign with the internal channel 460 such that the hole axis 526 is now substantially perpendicular to the channel axis 480 of the internal channel 460. In other words, the internal channel 460 is now closed restricting communication between the dual suction valves 410, 411 via the hole 525. This closing of the internal channel 460 allows suction to be applied to only one of the two valves 410, 411 and therefore to only one of the two corresponding working channels or ports.

As discussed earlier the valve switcher 420 can be turned/rotated about 45 degrees on either side of the longitudinal axis 425, in one embodiment. This means that, in one embodiment, the total angular rotation or turn of the valve switcher 420 is 90 degrees. Thus, while in the first position of FIG. 4f the hole axis 526 is substantially parallel to and approximately coinciding with the channel axis 480 of the internal channel 460; in the second position of FIG. 4g, which is 90 degrees rotated from the first position of FIG. 4f, the hole axis 526 is substantially perpendicular to the channel axis 480 of the internal channel 460. Persons of ordinary skill in the art should note that the angular turn or rotation of the valve switcher 420 of 45 degrees, on either side of the longitudinal axis 425, is only exemplary and could be different in alternate embodiments provided the switching from the first position to the second position and vice versa causes the through hole 525 to close or open the internal channel 460 for suction to be applied to any one or both of the dual suction valves 410, 411.

Figure 6A:
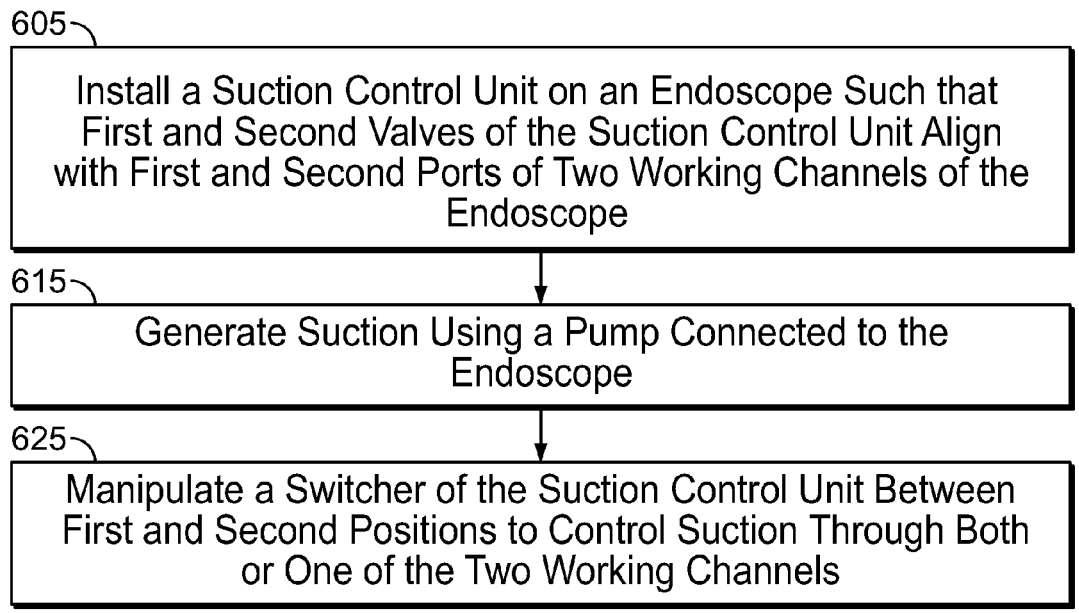
FIG. 6a is a flowchart illustrating a plurality of exemplary steps of a method of using the suction control unit or module of FIGS. 2a, 2b in accordance with an embodiment.

FIG. 6a is a flowchart illustrating a plurality of exemplary steps of a method of using the suction control unit or module 200 of FIGS. 2a, 2b in accordance with an embodiment. Referring now to FIG. 6a, along with FIGS. 2a through 2d and FIGS. 3a and 3b, at step 605 the suction control unit or module 200 is removably or fixedly installed, mounted, placed or attached on an endoscope such that the first and second valves 215, 216 of the module 200 are aligned with respective first and second ports (such as ports 111, 112 of FIG. 1) of two working channels of the endoscope. The through opening 240 extending from the front wall 203 to the rear wall 204 of the suction control unit 200 holds the shaft 310 of the valve switcher 220 (FIGS. 3a, 3b). At step 615, suction is generated using a pump connected to the endoscope. Thereafter, at step 625, the generated suction is controlled, using the suction control unit or module 200, so that suction is applied either through both the working channels or through just one of the two working channels. This is enabled by manipulating the valve switcher 220 to be in either the first position 230 on one side of the longitudinal axis 225 of the unit 200 or the second position 231 on another side of the longitudinal axis 225. Thus, when the valve switcher is in the first position 230, as shown in FIG. 2a, it causes an internal channel between the dual suction valves 210, 211 to open resulting in suction to be applied to both the valves 210, 211 and therefore to both corresponding working channels or ports. When the valve switcher 220 is turned/rotated to be in a second position 231, as shown in FIG. 2b, it causes the internal channel between the dual suction valves 210, 211 to close resulting in suction to be applied to only one of the two valves 210, 211 and therefore to only one out of the two corresponding working channels or ports.

Figure 6B:
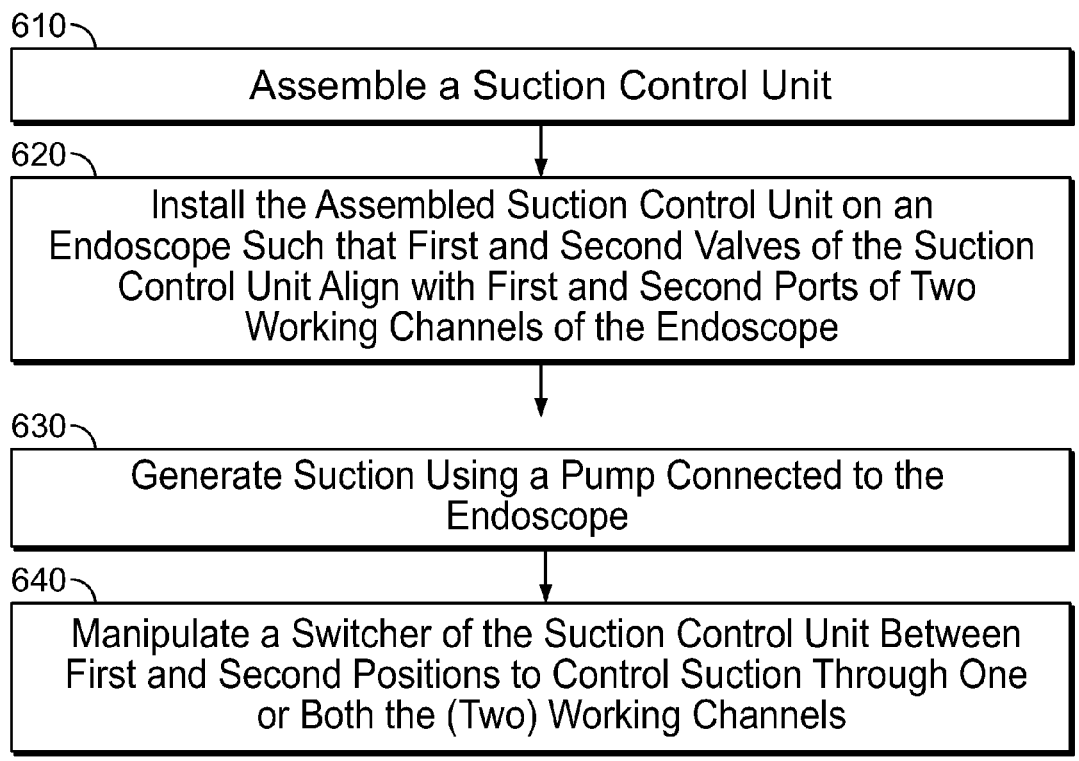
FIG. 6b is a flowchart illustrating a plurality of exemplary steps of a method of using the suction control unit or module of FIGS. 4b through 4e in accordance with an embodiment.

FIG. 6b is a flowchart illustrating a plurality of exemplary steps of a method of using the suction control unit or module 400 of FIGS. 4b through 4e in accordance with an embodiment. Referring now to FIG. 6b, along with FIGS. 4a through 4e and FIG. 5, at step 610 the suction control unit or module 400 is assembled by a) mounting the housing 405 over first and second valves 410, 411 such that first and second receptacle tubes 417, 418, hold the first and second valves 410, 411 therein and then by b) engaging/placing the valve switcher 420 in the opening 440 such that the shaft 510 of the switcher is held within the opening 440. The assembled suction control unit or module 400, at step 620, is removably or fixedly installed, mounted, placed or attached on an endoscope such that the first and second valves 410, 411 are aligned with respective first and second ports (such as ports 111, 112 of FIG. 1) of two working channels of the endoscope. The opening 440 extending from the front wall 403 to the rear wall 404 of the suction control unit 400 holds the shaft 510 of the valve switcher 420 (FIGS. 3a, 3b). At step 630, suction is generated using a pump connected to the endoscope. Thereafter, at step 640, the generated suction is controlled, using the suction control unit or module 400, so that suction is applied either through both the working channels or through just one of the two working channels. This is enabled by manipulating the valve switcher 420 to be in either the first position 445 on one side of the longitudinal axis 425 of the unit 400 or the second position 446 on another side of the longitudinal axis 425. Thus, when the valve switcher is in the first position 445, as shown in FIG. 4b, it causes an internal channel between the dual suction valves 410, 411 to close resulting in suction to be applied to only one of the two valves 410, 411 and therefore to only one out of the two corresponding working channels or ports. When the valve switcher 420 is turned/rotated to be in the second position 446, as shown in FIG. 4c, it causes the internal channel to open resulting in suction to be applied to both the valves 410, 411 and therefore to both corresponding working channels or ports.

The above examples are merely illustrative of the many applications of the suction unit of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A suction control unit configured to be detachably attached to at least two working channels of an endoscope and control application of suction through at least one of the two working channels, the suction unit comprising:
   a housing, defined by a central longitudinal axis, comprising:
     a first valve and a second valve positioned on either side of the central longitudinal axis, wherein a proximal end of the first and the second valve has respective first and second valve openings that lead through to a distal end of the first and the second valve, and wherein the distal end of the first and the second valve is configured to be detachably attached to first and second ports of the two working channels;
     a channel extending between the first and the second valve within the housing, wherein a channel axis is substantially perpendicular to the central longitudinal axis of the housing;
     an opening extending from a front wall to a rear wall of the housing and through the channel between the first and the second valve; and
   a switcher having a handle and a shaft extending from the handle along a long axis, wherein the shaft has a through hole such that a hole axis is substantially perpendicular to the long axis, wherein, when the shaft is placed within the opening and turned to a first position, the hole axis aligns with the channel and thereby opens the channel, enabling suction to be applied to both of the two working channels, and wherein, when the shaft is placed within the opening and turned to a second position, the shaft blocks the channel and causes suction to be applied to only one of the two working channels.

2. The suction control unit of claim 1, wherein the first and second positions are respectively at about 45 degrees on either side of the central longitudinal axis of the housing.

3. The suction control unit of claim 1, wherein switcher tracks are located on the front and the rear wall of the housing to restrict rotation of the switcher beyond said first and second positons.

4. The suction control unit of claim 1, wherein the first and second valve openings are aligned with respective first and second ports of the two working channels.

5. The suction control unit of claim 1, wherein the shaft of the switcher has a first surface that abuts against the front wall and a second surface that protrudes from and abuts against the rear wall.

6. The suction control unit of claim 5, wherein the first surface is ring shaped and the second surface has a semispherical shape.

7. The suction control unit of claim 5, wherein the first and second surfaces are ring shaped and wherein the second surface has an extension with two open rings to respectively hold two stoppers configured for the first and the second valve openings.

8. The suction control unit of claim 7, wherein the extension is cylindrical or rectangular.

9. The suction control unit of claim 1, wherein the handle of the switcher has an open ring to hold two stoppers configured for the first and the second valve openings.

10. The suction control unit of claim 1, wherein in the first position the hole axis is substantially parallel to the channel axis while in the second position the hole axis is substantially perpendicular to the channel axis.

11. The suction control unit of claim 1, wherein a surgical tool is inserted in one or both of the first and the second valve openings while suction is applied through one or both of the two working channels.

12. A suction control unit configured to be detachably attached to two working channels of an endoscope and control an application of suction through at least one of said two working channels, the suction unit comprising:
- first and second valves having a proximal end and a distal end, wherein the proximal end has first and second valve openings that lead through to the distal end, wherein the distal end retains first and second plugs, and wherein the distal end is adapted to be detachably attached to first and second ports of the two working channels;
- a housing comprising:
  - first and second receptacle tubes, on either side of a longitudinal axis of the housing, holding the first and second valves therein;
  - a channel extending between the first and second receptacle tubes to enable fluid communication between the first and second valves held within the first and second receptacle tubes, wherein a channel axis is substantially perpendicular to the longitudinal axis;
  - an opening extending from a front wall to a rear wall of the housing and through the channel; and
- a switcher having a handle and a shaft extending from the handle along a long axis, wherein the shaft has a plurality of pins and a through hole such that a hole axis is substantially perpendicular to the long axis, wherein the shaft is placed within the opening, and wherein a first position of the switcher causes suction to be applied to both the working channels and a second position of the switcher causes suction to be applied to one of the two working channels.

13. The suction control unit of claim 12, wherein the first and second positions are respectively at about 45 degrees on either side of the longitudinal axis of the housing.

14. The suction control unit of claim 12, wherein upper and lower tracks are located on at least the front wall to engage with said plurality of pins and restrict rotation of the switcher beyond said first and second positions.

15. The control unit of claim 12, wherein the first and second valve openings are aligned with respective first and second ports of the two working channels.

16. The suction control unit of claim 12, wherein the shaft of the switcher has a first surface that abuts against the front wall and a second surface that protrudes from and abuts against the rear wall.

17. The suction control unit of claim 16, wherein the first surface is ring shaped and the second surface has a semi-spherical shape.

18. The suction control unit of claim 16, wherein a first number of said plurality of pins abut against the first surface and a second number of said plurality of pins abut against the second surface.

19. The suction control unit of claim 12, wherein in the first position the hole axis is substantially parallel to the channel axis while in the second position the hole axis is substantially perpendicular to the channel axis.

20. The suction control unit of claim 12, wherein a surgical tool is inserted in one or both of the first and second valve openings while suction is applied through one or both of the two working channels.

21. The suction control unit of claim 12, wherein outer walls of the first and second valves have depressions to enable flush fit of the valves with the housing.

22. The suction control unit of claim 12, wherein the first and second valves, the housing and the switcher are separable into independent units.

* * * * *